(12) United States Patent  
Altarac et al.

(10) Patent No.: US 10,653,456 B2  
(45) Date of Patent: May 19, 2020

(54) INTERSPINOUS SPACER

(71) Applicant: VertiFlex, Inc., San Clemente, CA (US)

(72) Inventors: Moti Altarac, Irvine, CA (US); Shawn Tebbe, San Clemente, CA (US); Daniel H. Kim, Houston, TX (US)

(73) Assignee: VERTIFLEX, INC., San Clemente, CA (US)

( * ) Notice: Subject to any disclaimer, the term of this patent is extended or adjusted under 35 U.S.C. 154(b) by 0 days.

(21) Appl. No.: 15/397,516

(22) Filed: Jan. 3, 2017

(65) Prior Publication Data

US 2017/0273722 A1 Sep. 28, 2017

Related U.S. Application Data

(63) Continuation of application No. 14/488,175, filed on Sep. 16, 2014, now Pat. No. 9,532,812, which is a (Continued)

(51) Int. Cl.
*A61B 17/70* (2006.01)

(52) U.S. Cl.
CPC ...... *A61B 17/7067* (2013.01); *A61B 17/7065* (2013.01); *A61B 17/7076* (2013.01)

(58) Field of Classification Search
CPC combination set(s) only.
See application file for complete search history.

(56) References Cited

U.S. PATENT DOCUMENTS 2,248,054 A 7/1941 Becker
2,677,369 A 5/1954 Knowles
(Continued)

FOREIGN PATENT DOCUMENTS

CA 268461 A 2/1927
CN 2794456 Y 7/2006
(Continued)

OTHER PUBLICATIONS

ASNR Neuroradiology Patient Information website, Brain and Spine Imaging: A Patient's Guide to Neuroradiology; Myelography; http://www.asnr.org/patientinfo/procedures/myelography.shtml#sthash.sXIDOxWq.dpbs, Copyright 2012-2013.
(Continued)

*Primary Examiner* — Christopher D. Prone
(74) *Attorney, Agent, or Firm* — Lowe Graham Jones PLLC; Bruce E. Black

(57) ABSTRACT

An implantable spacer for placement between adjacent spinous processes in a spinal motion segment is provided. The spacer includes a body defining a longitudinal passageway. A first arm and a second arm are connected to the body. Each arm has a pair of extensions and a saddle defining a receiving portion configured for seating a spinous process of a scoliotic spine or a spine with misaligned spinous processes. Each arm has a proximal caming surface and is capable of rotation with respect to the body. An actuator assembly is disposed inside the longitudinal passageway and connected to the body. When advanced, a threaded shaft of the actuator assembly contacts the caming surfaces of arms to rotate them from an undeployed configuration to a deployed configuration. In the deployed configuration, the distracted adjacent spinous processes are seated in the superior and inferior arms of the spacer.

15 Claims, 15 Drawing Sheets

Related U.S. Application Data continuation of application No. 12/354,517, filed on Jan. 15, 2009, now Pat. No. 8,864,828.

(60) Provisional application No. 61/011,199, filed on Jan. 15, 2008.

(56) References Cited

U.S. PATENT DOCUMENTS

| | | |
|---|---|---|
| 2,933,114 A | 4/1960 | Bystrom |
| 3,242,120 A | 3/1966 | Steuber |
| 3,486,505 A | 12/1969 | Morrison |
| 3,648,691 A | 3/1972 | Lumb et al. |
| 3,780,733 A | 12/1973 | Martinez-Manzor |
| 3,986,383 A | 10/1976 | Petteys |
| 4,545,374 A | 10/1985 | Jacobson |
| 4,632,101 A | 12/1986 | Freedland |
| 4,685,447 A | 8/1987 | Iversen et al. |
| 4,799,484 A | 1/1989 | Smith et al. |
| 4,863,476 A | 9/1989 | Shepperd |
| 4,895,564 A | 1/1990 | Farrell |
| 4,986,831 A | 1/1991 | King et al. |
| 5,011,484 A | 4/1991 | Breard et al. |
| 5,015,247 A | 5/1991 | Michelson |
| 5,019,081 A | 5/1991 | Watanabe |
| 5,040,542 A | 8/1991 | Gray |
| 5,059,193 A | 10/1991 | Kuslich |
| 5,092,866 A | 3/1992 | Breard et al. |
| 5,178,628 A | 1/1993 | Otsuka et al. |
| 5,180,393 A | 1/1993 | Commarmond et al. |
| 5,182,281 A | 1/1993 | Frigola-Constansa et al. |
| 5,188,281 A | 2/1993 | Fujiwara et al. |
| 5,192,281 A | 3/1993 | de la Caffiniere |
| 5,195,526 A | 3/1993 | Michelson |
| 5,298,253 A | 3/1994 | LeFiles et al. |
| 5,368,594 A | 11/1994 | Martin et al. |
| 5,390,683 A | 2/1995 | Pisharodi |
| 5,415,661 A | 5/1995 | Holmes |
| 5,456,722 A | 10/1995 | McLeod et al. |
| 5,462,738 A | 10/1995 | LeFiles et al. |
| 5,472,452 A | 12/1995 | Trott |
| 5,484,437 A | 1/1996 | Michelson |
| 5,487,739 A | 1/1996 | Aebischer et al. |
| 5,489,308 A | 2/1996 | Kuslich et al. |
| 5,496,318 A | 3/1996 | Howland et al. |
| 5,531,748 A | 7/1996 | de la Caffiniere et al. |
| 5,549,679 A | 8/1996 | Kuslich |
| 5,571,189 A | 11/1996 | Kuslich |
| 5,591,165 A | 1/1997 | Jackson |
| 5,609,634 A | 3/1997 | Voydeville et al. |
| 5,609,636 A | 3/1997 | Kohrs et al. |
| 5,645,599 A * | 7/1997 | Samani ............ A61B 17/7062 606/248 |
| 5,654,599 A | 8/1997 | Casper |
| 5,658,335 A | 8/1997 | Allen |
| 5,658,337 A | 8/1997 | Kohrs et al. |
| 5,674,295 A | 10/1997 | Ray et al. |
| 5,700,264 A | 12/1997 | Zucherman et al. |
| 5,725,582 A | 3/1998 | Bevan et al. |
| 5,741,253 A | 4/1998 | Michelson |
| 5,746,720 A | 5/1998 | Stouder, Jr. |
| 5,762,629 A | 6/1998 | Kambin |
| 5,836,948 A | 11/1998 | Zucherman et al. |
| 5,860,977 A | 1/1999 | Zucherman et al. |
| 5,863,948 A | 1/1999 | Epstein et al. |
| 5,876,404 A | 3/1999 | Zucherman et al. |
| RE36,211 E | 5/1999 | Nonomura et al. |
| 5,904,636 A | 5/1999 | Chen et al. |
| 5,904,686 A | 5/1999 | Zucherman et al. |
| 5,928,207 A | 7/1999 | Pisano et al. |
| 5,948,017 A | 9/1999 | Taheri |
| 5,972,015 A | 10/1999 | Scribner et al. |
| 6,039,761 A | 3/2000 | Li et al. |
| 6,045,552 A | 4/2000 | Zucherman et al. |
| 6,048,342 A | 4/2000 | Zucherman et al. |
| 6,048,345 A | 4/2000 | Berke et al. |
| 6,066,154 A | 5/2000 | Reiley et al. |
| 6,068,630 A | 5/2000 | Zucherman et al. |
| 6,074,390 A | 6/2000 | Zucherman et al. |
| 6,080,155 A | 6/2000 | Michelson |
| 6,080,157 A | 6/2000 | Cathro et al. |
| 6,090,112 A | 7/2000 | Zucherman et al. |
| 6,096,038 A | 8/2000 | Michelson |
| 6,102,928 A | 8/2000 | Bonutti |
| D433,193 S | 10/2000 | Gaw et al. |
| 6,132,464 A | 10/2000 | Martin et al. |
| 6,149,642 A | 11/2000 | Gerhart et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,159,215 A | 12/2000 | Urbahns et al. |
| 6,179,873 B1 | 1/2001 | Zientek |
| 6,183,471 B1 | 2/2001 | Zucherman et al. |
| 6,190,387 B1 | 2/2001 | Zucherman et al. |
| 6,225,048 B1 | 5/2001 | Soderberg-Naucler et al. |
| 6,235,030 B1 | 5/2001 | Zucherman et al. |
| 6,238,397 B1 | 5/2001 | Zucherman et al. |
| 6,264,651 B1 | 7/2001 | Underwood et al. |
| 6,264,656 B1 | 7/2001 | Michelson |
| 6,267,763 B1 | 7/2001 | Castro |
| 6,267,765 B1 | 7/2001 | Taylor et al. |
| 6,270,498 B1 | 8/2001 | Michelson |
| 6,280,444 B1 | 8/2001 | Zucherman et al. |
| 6,312,431 B1 | 11/2001 | Asfora |
| 6,328,730 B1 | 12/2001 | Harkrider, Jr. |
| 6,332,882 B1 | 12/2001 | Zucherman et al. |
| 6,332,883 B1 | 12/2001 | Zucherman et al. |
| 6,336,930 B1 | 1/2002 | Stalcup et al. |
| 6,348,053 B1 | 2/2002 | Cachia |
| 6,364,883 B1 | 4/2002 | Santilli |
| 6,371,989 B1 | 4/2002 | Chauvin et al. |
| 6,375,682 B1 | 4/2002 | Fleischmann et al. |
| 6,379,355 B1 | 4/2002 | Zucherman et al. |
| 6,387,130 B1 | 5/2002 | Stone et al. |
| 6,395,032 B1 | 5/2002 | Gauchet et al. |
| 6,402,740 B1 | 6/2002 | Ellis et al. |
| 6,402,750 B1 | 6/2002 | Atkinson et al. |
| 6,402,784 B1 | 6/2002 | Wardlaw et al. |
| 6,413,228 B1 | 7/2002 | Hung et al. |
| 6,419,676 B1 | 7/2002 | Zucherman et al. |
| 6,419,677 B2 | 7/2002 | Zucherman et al. |
| 6,440,169 B1 * | 8/2002 | Elberg ............ A61B 17/7062 623/17.11 |
| 6,443,988 B2 | 9/2002 | Felt et al. |
| 6,447,547 B1 | 9/2002 | Michelson |
| 6,451,019 B1 | 9/2002 | Zucherman et al. |
| 6,451,020 B1 | 9/2002 | Zucherman et al. |
| 6,464,682 B1 | 10/2002 | Snoke |
| 6,471,976 B1 | 10/2002 | Taylor et al. |
| 6,478,796 B2 | 11/2002 | Zucherman et al. |
| 6,478,822 B1 | 11/2002 | Leroux et al. |
| 6,500,178 B2 | 12/2002 | Zucherman et al. |
| 6,514,256 B2 | 2/2003 | Zucherman et al. |
| 6,530,925 B2 | 3/2003 | Boudard et al. |
| 6,558,333 B2 | 5/2003 | Gilboa et al. |
| 6,565,570 B2 | 5/2003 | Sterett et al. |
| 6,572,617 B1 | 6/2003 | Senegas et al. |
| 6,575,981 B1 | 6/2003 | Boyd et al. |
| 6,579,281 B2 | 6/2003 | Palmer et al. |
| 6,579,319 B2 | 6/2003 | Goble et al. |
| 6,582,433 B2 | 6/2003 | Yun |
| 6,582,451 B1 | 6/2003 | Marucci et al. |
| 6,599,292 B1 | 7/2003 | Ray |
| 6,602,248 B1 | 8/2003 | Sharps et al. |
| 6,610,065 B1 | 8/2003 | Branch et al. |
| 6,610,091 B1 | 8/2003 | Reiley |
| 6,616,673 B1 | 9/2003 | Stone et al. |
| 6,626,944 B1 | 9/2003 | Taylor et al. |
| 6,645,207 B2 | 11/2003 | Dixon et al. |
| 6,645,211 B2 | 11/2003 | Magana |
| 6,652,527 B2 | 11/2003 | Zucherman et al. |
| 6,652,534 B2 | 11/2003 | Zucherman et al. |
| 6,663,637 B2 | 12/2003 | Dixon et al. |
| 6,679,886 B2 | 1/2004 | Weikel et al. |

(56) References Cited

U.S. PATENT DOCUMENTS

| | | |
|---|---|---|
| 6,695,842 B2 | 2/2004 | Zucherman et al. |
| 6,699,246 B2 | 3/2004 | Zucherman et al. |
| 6,699,247 B2 | 3/2004 | Zucherman et al. |
| 6,702,847 B2 | 3/2004 | DiCarlo |
| 6,712,819 B2 | 3/2004 | Zucherman et al. |
| 6,716,215 B1 | 4/2004 | David et al. |
| 6,716,245 B2 | 4/2004 | Pasquet et al. |
| 6,726,690 B2 | 4/2004 | Eckman |
| 6,733,534 B2 | 5/2004 | Sherman |
| 6,746,485 B1 | 6/2004 | Zucherman et al. |
| 6,761,720 B1 | 7/2004 | Senegas et al. |
| 6,783,529 B2 | 8/2004 | Hover et al. |
| 6,783,546 B2 | 8/2004 | Zucherman et al. |
| 6,796,983 B1 | 9/2004 | Zucherman et al. |
| 6,805,697 B1 | 10/2004 | Helm et al. |
| 6,835,205 B2 | 12/2004 | Atkinson et al. |
| 6,840,944 B2 | 1/2005 | Suddaby |
| 6,858,029 B2 | 2/2005 | Yeh |
| 6,869,398 B2 | 3/2005 | Obenchain et al. |
| 6,875,212 B2 | 4/2005 | Shaolian et al. |
| 6,902,566 B2 | 6/2005 | Zucherman et al. |
| 6,926,728 B2 | 8/2005 | Zucherman et al. |
| 6,946,000 B2 | 9/2005 | Senegas et al. |
| 6,949,123 B2 | 9/2005 | Reiley |
| 6,966,930 B2 | 11/2005 | Arnin et al. |
| 6,974,478 B2 | 12/2005 | Reiley et al. |
| 6,976,988 B2 | 12/2005 | Ralph et al. |
| 7,011,685 B2 | 3/2006 | Arnin et al. |
| 7,029,473 B2 | 4/2006 | Zucherman et al. |
| 7,033,358 B2 | 4/2006 | Taylor et al. |
| 7,048,736 B2 | 5/2006 | Robinson et al. |
| 7,070,598 B2 | 7/2006 | Lim et al. |
| 7,083,649 B2 | 8/2006 | Zucherman et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,101,375 B2 | 9/2006 | Zucherman et al. |
| 7,163,558 B2 | 1/2007 | Senegas et al. |
| 7,179,225 B2 | 2/2007 | Shluzas et al. |
| 7,187,064 B2 | 3/2007 | Tzu et al. |
| 7,189,234 B2 | 3/2007 | Zucherman et al. |
| 7,189,236 B2 | 3/2007 | Taylor et al. |
| 7,201,751 B2 | 4/2007 | Zucherman et al. |
| 7,217,291 B2 | 5/2007 | Zucherman et al. |
| 7,223,289 B2 | 5/2007 | Trieu et al. |
| 7,229,441 B2 | 6/2007 | Trieu et al. |
| 7,238,204 B2 | 7/2007 | Le Couedic et al. |
| 7,252,673 B2 | 8/2007 | Lim |
| 7,273,496 B2 | 9/2007 | Mitchell |
| 7,282,063 B2 | 10/2007 | Cohen et al. |
| 7,297,162 B2 | 11/2007 | Mujwid |
| 7,306,628 B2 | 12/2007 | Zucherman et al. |
| 7,318,839 B2 | 1/2008 | Malberg et al. |
| 7,320,707 B2 | 1/2008 | Zucherman et al. |
| 7,335,200 B2 | 2/2008 | Carli |
| 7,335,203 B2 | 2/2008 | Winslow et al. |
| 7,354,453 B2 | 4/2008 | McAfee |
| 7,384,340 B2 | 6/2008 | Eguchi et al. |
| 7,390,330 B2 | 6/2008 | Harp |
| 7,410,501 B2 | 8/2008 | Michelson |
| 7,442,208 B2 | 10/2008 | Mathieu et al. |
| 7,445,637 B2 | 11/2008 | Taylor |
| 7,473,268 B2 | 1/2009 | Zucherman et al. |
| 7,476,251 B2 | 1/2009 | Zucherman et al. |
| 7,481,839 B2 | 1/2009 | Zucherman et al. |
| 7,481,840 B2 | 1/2009 | Zucherman et al. |
| 7,491,204 B2 | 2/2009 | Marnay et al. |
| 7,497,859 B2 | 3/2009 | Zucherman et al. |
| 7,503,935 B2 | 3/2009 | Zucherman et al. |
| 7,504,798 B2 | 3/2009 | Kawada et al. |
| 7,510,567 B2 | 3/2009 | Zucherman et al. |
| 7,520,887 B2 | 4/2009 | Maxy et al. |
| 7,520,899 B2 | 4/2009 | Zucherman et al. |
| 7,547,308 B2 | 6/2009 | Bertagnoli et al. |
| 7,549,999 B2 | 6/2009 | Zucherman et al. |
| 7,550,009 B2 | 6/2009 | Arnin et al. |
| 7,565,259 B2 | 7/2009 | Sheng et al. |
| 7,572,276 B2 | 8/2009 | Lim et al. |
| 7,575,600 B2 | 8/2009 | Zucherman et al. |
| 7,585,313 B2 | 9/2009 | Kwak et al. |
| 7,585,316 B2 | 9/2009 | Trieu |
| 7,588,588 B2 | 9/2009 | Spitler et al. |
| 7,591,851 B2 | 9/2009 | Winslow et al. |
| 7,601,170 B2 | 10/2009 | Winslow et al. |
| 7,621,939 B2 | 11/2009 | Zucherman et al. |
| 7,635,377 B2 | 12/2009 | Zucherman et al. |
| 7,635,378 B2 | 12/2009 | Zucherman et al. |
| 7,637,950 B2 | 12/2009 | Baccelli et al. |
| 7,658,752 B2 | 2/2010 | Labrom et al. |
| 7,662,187 B2 | 2/2010 | Zucherman et al. |
| 7,666,186 B2 | 2/2010 | Harp |
| 7,666,209 B2 | 2/2010 | Zucherman et al. |
| 7,666,228 B2 | 2/2010 | Le Couedic et al. |
| 7,670,377 B2 | 3/2010 | Zucherman et al. |
| 7,682,376 B2 | 3/2010 | Trieu |
| 7,691,146 B2 | 4/2010 | Zucherman et al. |
| 7,695,513 B2 | 4/2010 | Zucherman et al. |
| 7,699,852 B2 | 4/2010 | Frankel et al. |
| 7,699,873 B2 | 4/2010 | Stevenson et al. |
| D618,796 S | 6/2010 | Cantu et al. |
| 7,727,233 B2 | 6/2010 | Blackwell et al. |
| 7,727,241 B2 | 6/2010 | Gorensek et al. |
| 7,731,751 B2 | 6/2010 | Butler et al. |
| 7,742,795 B2 | 6/2010 | Stone et al. |
| 7,749,231 B2 | 7/2010 | Bonvallet et al. |
| 7,749,252 B2 | 7/2010 | Zucherman et al. |
| 7,749,253 B2 | 7/2010 | Zucherman et al. |
| 7,753,938 B2 | 7/2010 | Aschmann et al. |
| 7,758,619 B2 | 7/2010 | Zucherman et al. |
| 7,758,647 B2 | 7/2010 | Arnin et al. |
| 7,763,028 B2 | 7/2010 | Lim et al. |
| 7,763,050 B2 | 7/2010 | Winslow et al. |
| 7,763,051 B2 | 7/2010 | Labrom et al. |
| 7,763,073 B2 | 7/2010 | Hawkins et al. |
| 7,763,074 B2 | 7/2010 | Altarac et al. |
| 7,766,967 B2 | 8/2010 | Francis |
| 7,776,090 B2 | 8/2010 | Winslow et al. |
| 7,780,709 B2 | 8/2010 | Bruneau et al. |
| 7,789,898 B2 | 9/2010 | Peterman |
| 7,794,476 B2 | 9/2010 | Wisnewski |
| 7,803,190 B2 | 9/2010 | Zucherman et al. |
| 7,806,911 B2 | 10/2010 | Peckham |
| 7,811,308 B2 | 10/2010 | Arnin et al. |
| 7,811,322 B2 | 10/2010 | Arnin et al. |
| 7,811,323 B2 | 10/2010 | Arnin et al. |
| 7,811,324 B2 | 10/2010 | Arnin et al. |
| 7,811,330 B2 | 10/2010 | Arnin et al. |
| 7,819,921 B2 | 10/2010 | Grotz |
| 7,828,822 B2 | 11/2010 | Zucherman et al. |
| 7,828,849 B2 | 11/2010 | Lim |
| 7,833,272 B2 | 11/2010 | Arnin et al. |
| 7,837,687 B2 | 11/2010 | Harp |
| 7,837,688 B2 | 11/2010 | Boyer, II et al. |
| 7,837,700 B2 | 11/2010 | Harp |
| 7,837,711 B2 | 11/2010 | Bruneau et al. |
| 7,837,734 B2 | 11/2010 | Zucherman et al. |
| 7,846,183 B2 | 12/2010 | Blain |
| 7,846,185 B2 | 12/2010 | Cads et al. |
| 7,846,186 B2 | 12/2010 | Taylor |
| 7,857,815 B2 | 12/2010 | Zucherman et al. |
| 7,862,569 B2 | 1/2011 | Zucherman et al. |
| 7,862,586 B2 | 1/2011 | Malek |
| 7,862,590 B2 | 1/2011 | Lim et al. |
| 7,862,592 B2 | 1/2011 | Peterson et al. |
| 7,862,615 B2 | 1/2011 | Carli et al. |
| 7,867,276 B2 | 1/2011 | Matge et al. |
| 7,871,426 B2 | 1/2011 | Chin et al. |
| 7,896,879 B2 | 3/2011 | Solsberg et al. |
| 7,942,830 B2 | 5/2011 | Solsberg et al. |
| 7,955,392 B2 | 6/2011 | Dewey et al. |
| 7,985,246 B2 | 7/2011 | Trieu |
| 8,012,207 B2 | 9/2011 | Kim |
| 8,025,684 B2 | 9/2011 | Garcia-Bengochea et al. |
| 8,057,513 B2 | 11/2011 | Kohm et al. |

(56) References Cited

U.S. PATENT DOCUMENTS

| | | |
|---|---|---|
| 8,062,332 B2 | 11/2011 | Cunningham et al. |
| 8,100,823 B2 | 1/2012 | Harp |
| 8,123,782 B2 | 2/2012 | Altarac et al. |
| 8,123,807 B2 | 2/2012 | Kim |
| 8,128,662 B2 | 3/2012 | Altarac et al. |
| 8,152,837 B2 | 4/2012 | Altarac et al. |
| 8,167,944 B2 | 5/2012 | Kim |
| 8,226,690 B2 | 7/2012 | Altarac et al. |
| 8,273,108 B2 | 9/2012 | Altarac et al. |
| 8,277,488 B2 | 10/2012 | Altarac et al. |
| 8,292,922 B2 | 10/2012 | Altarac et al. |
| 8,317,864 B2 | 11/2012 | Kim |
| 8,409,282 B2 | 4/2013 | Kim |
| 8,425,559 B2 | 4/2013 | Tebbe et al. |
| 8,608,762 B2 | 12/2013 | Solsberg et al. |
| 8,613,747 B2 | 12/2013 | Altarac et al. |
| 8,628,574 B2 | 1/2014 | Altarac et al. |
| 8,696,671 B2 | 4/2014 | Solsberg et al. |
| 8,734,477 B2 | 5/2014 | Solsberg et al. |
| 8,740,948 B2 | 6/2014 | Reglos et al. |
| 8,845,726 B2 | 9/2014 | Tebbe et al. |
| 8,864,828 B2 | 10/2014 | Altarac et al. |
| 8,882,772 B2 | 11/2014 | Solsberg et al. |
| 8,894,653 B2 | 11/2014 | Solsberg et al. |
| 8,900,271 B2 | 12/2014 | Kim |
| 8,945,183 B2 | 2/2015 | Altarac et al. |
| 9,023,084 B2 | 5/2015 | Kim |
| 9,039,742 B2 | 5/2015 | Altarac et al. |
| 9,119,680 B2 | 9/2015 | Altarac et al. |
| 9,125,692 B2 | 9/2015 | Kim |
| 9,155,570 B2 | 10/2015 | Altarac et al. |
| 9,155,572 B2 | 10/2015 | Altarac et al. |
| 9,161,783 B2 | 10/2015 | Altarac et al. |
| 9,186,186 B2 | 11/2015 | Reglos et al. |
| 9,211,146 B2 | 12/2015 | Kim |
| 9,283,005 B2 | 3/2016 | Tebbe et al. |
| 9,314,279 B2 | 4/2016 | Kim |
| 9,393,055 B2 | 7/2016 | Altarac et al. |
| 9,445,843 B2 | 9/2016 | Altarac et al. |
| 9,532,812 B2 | 1/2017 | Altarac et al. |
| 9,572,603 B2 | 2/2017 | Altarac et al. |
| 9,675,303 B2 | 6/2017 | Choi et al. |
| 2001/0031965 A1 | 10/2001 | Zucherman et al. |
| 2002/0022856 A1 | 2/2002 | Johnson et al. |
| 2002/0042607 A1 | 4/2002 | Palmer et al. |
| 2002/0116009 A1 | 8/2002 | Fraser |
| 2002/0143331 A1 | 10/2002 | Zucherman et al. |
| 2002/0151977 A1 | 10/2002 | Paes et al. |
| 2003/0040746 A1 | 2/2003 | Mitchell et al. |
| 2003/0040753 A1 | 2/2003 | Daum et al. |
| 2003/0074075 A1 | 4/2003 | Thomas et al. |
| 2003/0105466 A1 | 6/2003 | Ralph et al. |
| 2003/0149438 A1 | 8/2003 | Nichols et al. |
| 2003/0153976 A1 | 8/2003 | Cauthen et al. |
| 2003/0176921 A1 | 9/2003 | Lawson |
| 2003/0220643 A1 | 11/2003 | Ferree |
| 2003/0220650 A1 | 11/2003 | Major et al. |
| 2003/0233098 A1 | 12/2003 | Markworth |
| 2004/0087947 A1 | 5/2004 | Lim et al. |
| 2004/0106997 A1 | 6/2004 | Lieberson |
| 2004/0106999 A1 | 6/2004 | Mathews |
| 2004/0148028 A1 | 7/2004 | Ferree |
| 2004/0167625 A1 | 8/2004 | Beyar et al. |
| 2004/0220568 A1 | 11/2004 | Zucherman et al. |
| 2004/0225295 A1 | 11/2004 | Zubok et al. |
| 2005/0021042 A1 | 1/2005 | Marnay |
| 2005/0049708 A1 | 3/2005 | Atkinson et al. |
| 2005/0075634 A1 | 4/2005 | Zucherman et al. |
| 2005/0090822 A1 | 4/2005 | DiPoto |
| 2005/0101955 A1 | 5/2005 | Zucherman et al. |
| 2005/0125066 A1 | 6/2005 | McAfee |
| 2005/0143738 A1 | 6/2005 | Zucherman et al. |
| 2005/0165398 A1 | 7/2005 | Reiley |
| 2005/0192586 A1 | 9/2005 | Zucherman et al. |
| 2005/0192671 A1 | 9/2005 | Bao et al. |
| 2005/0209603 A1 | 9/2005 | Zucherman et al. |
| 2005/0209698 A1 | 9/2005 | Gordon |
| 2005/0216087 A1 | 9/2005 | Zucherman et al. |
| 2005/0228383 A1 | 10/2005 | Zucherman et al. |
| 2005/0228384 A1 | 10/2005 | Zucherman et al. |
| 2005/0228426 A1 | 10/2005 | Campbell |
| 2005/0245937 A1 | 11/2005 | Winslow |
| 2005/0278036 A1 | 12/2005 | Leonard et al. |
| 2006/0030860 A1 | 2/2006 | Peterman |
| 2006/0036258 A1 | 2/2006 | Zucherman et al. |
| 2006/0064107 A1 | 3/2006 | Bertagnoli et al. |
| 2006/0064165 A1 | 3/2006 | Zucherman et al. |
| 2006/0064166 A1 | 3/2006 | Zucherman et al. |
| 2006/0074431 A1 | 4/2006 | Sutton et al. |
| 2006/0084976 A1 | 4/2006 | Borgstrom et al. |
| 2006/0084983 A1 | 4/2006 | Kim |
| 2006/0084985 A1 | 4/2006 | Kim |
| 2006/0084988 A1 | 4/2006 | Kim |
| 2006/0084991 A1 | 4/2006 | Borgstrom et al. |
| 2006/0085069 A1 | 4/2006 | Kim |
| 2006/0085070 A1 | 4/2006 | Kim |
| 2006/0085074 A1 | 4/2006 | Raiszadeh |
| 2006/0089718 A1 | 4/2006 | Zucherman et al. |
| 2006/0122458 A1 | 6/2006 | Bleich |
| 2006/0122620 A1 | 6/2006 | Kim |
| 2006/0129239 A1* | 6/2006 | Kwak ............... A61B 17/7064 623/17.13 |
| 2006/0149254 A1 | 7/2006 | Lauryssen et al. |
| 2006/0149289 A1 | 7/2006 | Winslow et al. |
| 2006/0167416 A1 | 7/2006 | Mathis et al. |
| 2006/0195102 A1 | 8/2006 | Malandain |
| 2006/0217811 A1 | 9/2006 | Lambrecht et al. |
| 2006/0224159 A1 | 10/2006 | Anderson |
| 2006/0235386 A1 | 10/2006 | Anderson |
| 2006/0241597 A1 | 10/2006 | Mitchell et al. |
| 2006/0241614 A1 | 10/2006 | Bruneau et al. |
| 2006/0241757 A1 | 10/2006 | Anderson |
| 2006/0247623 A1 | 11/2006 | Anderson et al. |
| 2006/0247632 A1 | 11/2006 | Winslow et al. |
| 2006/0247633 A1 | 11/2006 | Winslow et al. |
| 2006/0247650 A1 | 11/2006 | Yerby et al. |
| 2006/0247773 A1 | 11/2006 | Stamp |
| 2006/0264938 A1 | 11/2006 | Zucherman et al. |
| 2006/0264939 A1 | 11/2006 | Zucherman et al. |
| 2006/0265066 A1 | 11/2006 | Zucherman et al. |
| 2006/0265067 A1 | 11/2006 | Zucherman et al. |
| 2006/0271044 A1 | 11/2006 | Petrini et al. |
| 2006/0271049 A1 | 11/2006 | Zucherman et al. |
| 2006/0271055 A1 | 11/2006 | Thramann |
| 2006/0271061 A1 | 11/2006 | Beyar et al. |
| 2006/0271194 A1 | 11/2006 | Zucherman et al. |
| 2006/0276801 A1 | 12/2006 | Yerby et al. |
| 2006/0276897 A1 | 12/2006 | Winslow et al. |
| 2006/0282077 A1 | 12/2006 | Labrom et al. |
| 2006/0282078 A1 | 12/2006 | Labrom et al. |
| 2007/0016196 A1 | 1/2007 | Winslow et al. |
| 2007/0055237 A1 | 3/2007 | Edidin et al. |
| 2007/0055246 A1 | 3/2007 | Zucherman et al. |
| 2007/0073289 A1 | 3/2007 | Kwak et al. |
| 2007/0100340 A1 | 5/2007 | Lange et al. |
| 2007/0100366 A1 | 5/2007 | Dziedzic et al. |
| 2007/0123863 A1 | 5/2007 | Winslow et al. |
| 2007/0123904 A1 | 5/2007 | Stad et al. |
| 2007/0161991 A1 | 7/2007 | Altarac et al. |
| 2007/0161993 A1 | 7/2007 | Lowery et al. |
| 2007/0173818 A1 | 7/2007 | Hestad et al. |
| 2007/0173821 A1 | 7/2007 | Trieu |
| 2007/0173822 A1 | 7/2007 | Bruneau et al. |
| 2007/0173823 A1 | 7/2007 | Dewey et al. |
| 2007/0173832 A1 | 7/2007 | Tebbe et al. |
| 2007/0173939 A1 | 7/2007 | Kim et al. |
| 2007/0179500 A1 | 8/2007 | Chin et al. |
| 2007/0185490 A1 | 8/2007 | Implicito |
| 2007/0191857 A1 | 8/2007 | Allard et al. |
| 2007/0191948 A1 | 8/2007 | Arnin et al. |
| 2007/0191991 A1 | 8/2007 | Addink |
| 2007/0198045 A1 | 8/2007 | Morton et al. |
| 2007/0198091 A1 | 8/2007 | Boyer et al. |
| 2007/0203493 A1 | 8/2007 | Zucherman et al. |

(56) References Cited

U.S. PATENT DOCUMENTS

| | | |
|---|---|---|
| 2007/0203495 A1 | 8/2007 | Zucherman et al. |
| 2007/0203496 A1 | 8/2007 | Zucherman et al. |
| 2007/0203497 A1 | 8/2007 | Zucherman et al. |
| 2007/0203501 A1 | 8/2007 | Zucherman et al. |
| 2007/0208345 A1 | 9/2007 | Marnay et al. |
| 2007/0208346 A1 | 9/2007 | Marnay et al. |
| 2007/0208366 A1 | 9/2007 | Pellegrino et al. |
| 2007/0210018 A1 | 9/2007 | Wallwiener et al. |
| 2007/0225706 A1 | 9/2007 | Clark et al. |
| 2007/0225724 A1 | 9/2007 | Edmond |
| 2007/0225807 A1 | 9/2007 | Phan et al. |
| 2007/0225814 A1 | 9/2007 | Atkinson et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233077 A1 | 10/2007 | Khalili |
| 2007/0233081 A1 | 10/2007 | Pasquet et al. |
| 2007/0233082 A1 | 10/2007 | Chin et al. |
| 2007/0233083 A1 | 10/2007 | Abdou |
| 2007/0233084 A1 | 10/2007 | Betz et al. |
| 2007/0233088 A1 | 10/2007 | Edmond |
| 2007/0233089 A1 | 10/2007 | DiPoto et al. |
| 2007/0233096 A1 | 10/2007 | Garcia-Bengochea |
| 2007/0233098 A1 | 10/2007 | Mastrorio et al. |
| 2007/0233129 A1 | 10/2007 | Bertagnoli et al. |
| 2007/0250060 A1 | 10/2007 | Anderson et al. |
| 2007/0260245 A1 | 11/2007 | Malandain et al. |
| 2007/0265623 A1 | 11/2007 | Malandain et al. |
| 2007/0265624 A1 | 11/2007 | Zucherman et al. |
| 2007/0265625 A1 | 11/2007 | Zucherman et al. |
| 2007/0265626 A1 | 11/2007 | Seme |
| 2007/0270822 A1 | 11/2007 | Heinz |
| 2007/0270823 A1 | 11/2007 | Trieu et al. |
| 2007/0270824 A1 | 11/2007 | Lim et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Cads et al. |
| 2007/0270834 A1 | 11/2007 | Bruneau et al. |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276372 A1 | 11/2007 | Malandain et al. |
| 2007/0276373 A1 | 11/2007 | Malandain |
| 2007/0276390 A1 | 11/2007 | Solsberg et al. |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0276500 A1 | 11/2007 | Zucherman et al. |
| 2008/0015700 A1 | 1/2008 | Zucherman et al. |
| 2008/0021468 A1 | 1/2008 | Zucherman et al. |
| 2008/0021560 A1 | 1/2008 | Zucherman et al. |
| 2008/0021561 A1 | 1/2008 | Zucherman et al. |
| 2008/0027545 A1 | 1/2008 | Zucherman et al. |
| 2008/0027552 A1 | 1/2008 | Zucherman et al. |
| 2008/0027553 A1 | 1/2008 | Zucherman et al. |
| 2008/0033445 A1 | 2/2008 | Zucherman et al. |
| 2008/0033553 A1 | 2/2008 | Zucherman et al. |
| 2008/0033558 A1 | 2/2008 | Zucherman et al. |
| 2008/0033559 A1 | 2/2008 | Zucherman et al. |
| 2008/0039853 A1 | 2/2008 | Zucherman et al. |
| 2008/0039858 A1 | 2/2008 | Zucherman et al. |
| 2008/0039859 A1 | 2/2008 | Zucherman et al. |
| 2008/0039945 A1 | 2/2008 | Zucherman et al. |
| 2008/0039946 A1 | 2/2008 | Zucherman et al. |
| 2008/0039947 A1 | 2/2008 | Zucherman et al. |
| 2008/0045958 A1 | 2/2008 | Zucherman et al. |
| 2008/0045959 A1 | 2/2008 | Zucherman et al. |
| 2008/0046081 A1 | 2/2008 | Zucherman et al. |
| 2008/0046085 A1 | 2/2008 | Zucherman et al. |
| 2008/0046086 A1 | 2/2008 | Zucherman et al. |
| 2008/0046087 A1 | 2/2008 | Zucherman et al. |
| 2008/0046088 A1 | 2/2008 | Zucherman et al. |
| 2008/0051785 A1 | 2/2008 | Zucherman et al. |
| 2008/0051896 A1 | 2/2008 | Suddaby |
| 2008/0051898 A1 | 2/2008 | Zucherman et al. |
| 2008/0051899 A1 | 2/2008 | Zucherman et al. |
| 2008/0051904 A1 | 2/2008 | Zucherman et al. |
| 2008/0051905 A1 | 2/2008 | Zucherman et al. |
| 2008/0058806 A1 | 3/2008 | Klyce et al. |
| 2008/0058807 A1 | 3/2008 | Klyce et al. |
| 2008/0058808 A1 | 3/2008 | Klyce et al. |
| 2008/0058941 A1 | 3/2008 | Zucherman et al. |
| 2008/0065086 A1 | 3/2008 | Zucherman et al. |
| 2008/0065212 A1 | 3/2008 | Zucherman et al. |
| 2008/0065213 A1 | 3/2008 | Zucherman et al. |
| 2008/0065214 A1 | 3/2008 | Zucherman et al. |
| 2008/0071280 A1 | 3/2008 | Winslow |
| 2008/0071378 A1 | 3/2008 | Zucherman et al. |
| 2008/0071380 A1 | 3/2008 | Sweeney |
| 2008/0086212 A1 | 4/2008 | Zucherman et al. |
| 2008/0108990 A1 | 5/2008 | Mitchell et al. |
| 2008/0114455 A1 | 5/2008 | Lange et al. |
| 2008/0132952 A1 | 6/2008 | Malandain et al. |
| 2008/0167655 A1 | 7/2008 | Wang et al. |
| 2008/0167656 A1 | 7/2008 | Zucherman et al. |
| 2008/0172057 A1 | 7/2008 | Zucherman et al. |
| 2008/0177271 A1* | 7/2008 | Yeh .............. A61B 17/7065 606/90 |
| 2008/0177272 A1 | 7/2008 | Zucherman et al. |
| 2008/0177306 A1 | 7/2008 | Lamborne et al. |
| 2008/0177312 A1 | 7/2008 | Perez-Cruet et al. |
| 2008/0183210 A1 | 7/2008 | Zucherman et al. |
| 2008/0188895 A1 | 8/2008 | Cragg et al. |
| 2008/0208344 A1 | 8/2008 | Kilpela et al. |
| 2008/0215058 A1 | 9/2008 | Zucherman et al. |
| 2008/0221692 A1 | 9/2008 | Zucherman et al. |
| 2008/0228225 A1 | 9/2008 | Trautwein et al. |
| 2008/0234708 A1 | 9/2008 | Houser et al. |
| 2008/0234824 A1 | 9/2008 | Youssef et al. |
| 2008/0288075 A1 | 11/2008 | Zucherman et al. |
| 2008/0319550 A1 | 12/2008 | Altarac et al. |
| 2009/0012528 A1 | 1/2009 | Aschmann et al. |
| 2009/0118833 A1 | 5/2009 | Hudgins et al. |
| 2009/0125030 A1 | 5/2009 | Tebbe et al. |
| 2009/0125036 A1 | 5/2009 | Bleich |
| 2009/0138046 A1 | 5/2009 | Altarac et al. |
| 2009/0138055 A1 | 5/2009 | Altarac et al. |
| 2009/0222043 A1 | 9/2009 | Altarac et al. |
| 2009/0248079 A1 | 10/2009 | Kwak et al. |
| 2009/0292315 A1 | 11/2009 | Trieu |
| 2010/0042217 A1 | 2/2010 | Zucherman et al. |
| 2010/0082108 A1 | 4/2010 | Zucherman et al. |
| 2010/0114100 A1 | 5/2010 | Mehdizade |
| 2010/0131009 A1 | 5/2010 | Roebling et al. |
| 2010/0160947 A1 | 6/2010 | Akyuz et al. |
| 2010/0228092 A1 | 9/2010 | Ortiz et al. |
| 2010/0234889 A1 | 9/2010 | Hess |
| 2010/0262243 A1 | 10/2010 | Zucherman et al. |
| 2010/0280551 A1 | 11/2010 | Pool et al. |
| 2010/0305611 A1 | 12/2010 | Zucherman et al. |
| 2011/0245833 A1 | 10/2011 | Anderson |
| 2011/0313457 A1 | 12/2011 | Reglos et al. |
| 2012/0078301 A1 | 3/2012 | Hess |
| 2012/0158063 A1 | 6/2012 | Altarac et al. |
| 2012/0226315 A1 | 9/2012 | Altarac et al. |
| 2012/0232552 A1 | 9/2012 | Morgenstern Lopez et al. |
| 2012/0303039 A1 | 11/2012 | Chin et al. |
| 2012/0330359 A1 | 12/2012 | Kim |
| 2013/0012998 A1 | 1/2013 | Altarac et al. |
| 2013/0072985 A1 | 3/2013 | Kim |
| 2013/0165974 A1 | 6/2013 | Kim |
| 2013/0165975 A1 | 6/2013 | Tebbe et al. |
| 2013/0172932 A1 | 7/2013 | Altarac et al. |
| 2013/0172933 A1 | 7/2013 | Altarac et al. |
| 2013/0289399 A1 | 10/2013 | Choi et al. |
| 2013/0289622 A1 | 10/2013 | Kim |
| 2014/0081332 A1 | 3/2014 | Altarac et al. |
| 2014/0214082 A1 | 7/2014 | Reglos et al. |
| 2015/0150598 A1 | 6/2015 | Tebbe et al. |
| 2015/0150604 A1 | 6/2015 | Kim |
| 2015/0374415 A1 | 12/2015 | Kim |
| 2016/0030092 A1 | 2/2016 | Altarac et al. |
| 2016/0045232 A1 | 2/2016 | Altarac et al. |

(56) References Cited

U.S. PATENT DOCUMENTS

| | | | |
|---|---|---|---|
| 2016/0066963 A1 | 3/2016 | Kim | |
| 2016/0135853 A1 | 5/2016 | Altarac et al. | |
| 2016/0248222 A1 | 8/2016 | Miyata | |
| 2016/0317193 A1 | 11/2016 | Kim | |
| 2017/0071588 A1 | 3/2017 | Choi et al. | |
| 2017/0128110 A1 | 5/2017 | Altarac et al. | |
| 2017/0156763 A1 | 6/2017 | Altarac et al. | |
| 2017/0245883 A1 | 8/2017 | Tebbe et al. | |
| 2017/0258501 A1 | 9/2017 | Altarac et al. | |
| 2018/0028130 A1 | 2/2018 | Choi | |
| 2018/0193064 A1 | 7/2018 | Kim | |

FOREIGN PATENT DOCUMENTS

| | | |
|---|---|---|
| CN | 101897603 | 12/2010 |
| DE | 69507480 | 9/1999 |
| EP | 322334 | 6/1989 |
| EP | 0767636 | 4/1997 |
| EP | 0768843 B1 | 4/1997 |
| EP | 0959792 B1 | 12/1999 |
| EP | 1027004 A1 | 8/2000 |
| EP | 1030615 A1 | 8/2000 |
| EP | 1138268 | 10/2001 |
| EP | 1330987 A1 | 7/2003 |
| EP | 1056408 B1 | 12/2003 |
| EP | 1343424 B1 | 9/2004 |
| EP | 1454589 A1 | 9/2004 |
| EP | 1148850 B1 | 4/2005 |
| EP | 1570793 A2 | 9/2005 |
| EP | 1299042 B1 | 3/2006 |
| EP | 1578314 B1 | 5/2007 |
| EP | 1675535 B1 | 5/2007 |
| EP | 1861046 A2 | 12/2007 |
| FR | 2681525 A1 | 3/1993 |
| FR | 2717675 A1 | 3/1994 |
| FR | 2722980 A1 | 2/1996 |
| FR | 2816197 A1 | 5/2002 |
| FR | 2884136 A1 | 10/2006 |
| FR | 2888744 A1 | 1/2007 |
| SU | 988281 A1 | 1/1983 |
| WO | WO-9404088 A1 | 3/1994 |
| WO | WO-9426192 A1 | 11/1994 |
| WO | WO-9525485 A1 | 9/1995 |
| WO | WO-9531158 A1 | 11/1995 |
| WO | WO-9600049 A1 | 1/1996 |
| WO | WO-9829047 A1 | 7/1998 |
| WO | WO-9921500 A1 | 5/1999 |
| WO | WO-9921501 A1 | 5/1999 |
| WO | WO-9942051 A1 | 8/1999 |
| WO | WO-0013619 A1 | 3/2000 |
| WO | WO-0044319 A1 | 8/2000 |
| WO | WO-0044321 A2 | 8/2000 |
| WO | WO-0128442 A1 | 4/2001 |
| WO | WO-0191657 A1 | 12/2001 |
| WO | WO-0191658 A1 | 12/2001 |
| WO | WO-0203882 A2 | 1/2002 |
| WO | WO-0207623 A1 | 1/2002 |
| WO | WO-0207624 A1 | 1/2002 |
| WO | WO-02051326 A1 | 7/2002 |
| WO | WO-02067793 A2 | 9/2002 |
| WO | WO-02071960 A1 | 9/2002 |
| WO | WO-02076336 A2 | 10/2002 |
| WO | WO-03007791 A2 | 1/2003 |
| WO | WO-03007829 A1 | 1/2003 |
| WO | WO-03008016 A2 | 1/2003 |
| WO | WO-03015646 A2 | 2/2003 |
| WO | WO-03024298 A2 | 3/2003 |
| WO | WO-03045262 A2 | 6/2003 |
| WO | WO-03099147 A1 | 12/2003 |
| WO | WO-03101350 A1 | 12/2003 |
| WO | WO-04073533 A1 | 9/2004 |
| WO | WO-04110300 A2 | 12/2004 |
| WO | WO-05009300 A1 | 2/2005 |
| WO | WO-05013839 A2 | 2/2005 |
| WO | WO-05025461 A2 | 3/2005 |
| WO | WO-05041799 A1 | 5/2005 |
| WO | WO-05044152 A1 | 5/2005 |
| WO | WO-05055868 A2 | 6/2005 |
| WO | WO-05079672 A2 | 9/2005 |
| WO | WO-2005086776 A2 | 9/2005 |
| WO | WO-05115261 A1 | 12/2005 |
| WO | WO-06033659 A2 | 3/2006 |
| WO | WO-06034423 A2 | 3/2006 |
| WO | WO-06039243 | 4/2006 |
| WO | WO-06039260 A2 | 4/2006 |
| WO | WO-06045094 A2 | 4/2006 |
| WO | WO-2006045094 A2 | 4/2006 |
| WO | WO-06063047 A2 | 6/2006 |
| WO | WO-06065774 A1 | 6/2006 |
| WO | WO-2006063047 A2 | 6/2006 |
| WO | WO-2006064356 A1 | 6/2006 |
| WO | WO-2006089085 A2 | 8/2006 |
| WO | WO-06102269 A2 | 9/2006 |
| WO | WO-06102428 A1 | 9/2006 |
| WO | WO-06102485 A2 | 9/2006 |
| WO | WO-06107539 A1 | 10/2006 |
| WO | WO-06110462 A2 | 10/2006 |
| WO | WO-06110464 A1 | 10/2006 |
| WO | WO-06110767 A1 | 10/2006 |
| WO | WO-06113080 A2 | 10/2006 |
| WO | WO-06113406 A2 | 10/2006 |
| WO | WO-06113814 A2 | 10/2006 |
| WO | WO-06118945 A1 | 11/2006 |
| WO | WO-06119235 A1 | 11/2006 |
| WO | WO-06119236 A2 | 11/2006 |
| WO | WO-06135511 A1 | 12/2006 |
| WO | WO-07015028 A1 | 2/2007 |
| WO | WO-07035120 A1 | 3/2007 |
| WO | WO-07075375 A2 | 7/2007 |
| WO | WO-07075788 A2 | 7/2007 |
| WO | WO-07075791 A2 | 7/2007 |
| WO | WO-07089605 A2 | 8/2007 |
| WO | WO-07089905 A2 | 8/2007 |
| WO | WO-07089975 A1 | 8/2007 |
| WO | WO-07097735 A2 | 8/2007 |
| WO | WO-07109402 A2 | 9/2007 |
| WO | WO-07110604 A1 | 10/2007 |
| WO | WO-07111795 A1 | 10/2007 |
| WO | WO-07111979 A2 | 10/2007 |
| WO | WO-07111999 A2 | 10/2007 |
| WO | WO-07117882 A1 | 10/2007 |
| WO | WO-07121070 A2 | 10/2007 |
| WO | WO-07127550 A2 | 11/2007 |
| WO | WO-07127588 A1 | 11/2007 |
| WO | WO-07127677 A1 | 11/2007 |
| WO | WO-07127689 A2 | 11/2007 |
| WO | WO-07127694 A2 | 11/2007 |
| WO | WO-07127734 A2 | 11/2007 |
| WO | WO-07127736 A2 | 11/2007 |
| WO | WO-07131165 A2 | 11/2007 |
| WO | WO-07134113 A2 | 11/2007 |
| WO | WO-2008009049 A1 | 1/2008 |
| WO | WO-08048645 A2 | 4/2008 |
| WO | WO-2008057506 A2 | 5/2008 |
| WO | WO-2008130564 A1 | 10/2008 |
| WO | WO-2009014728 A2 | 1/2009 |
| WO | WO-2009033093 A1 | 3/2009 |
| WO | WO-2009086010 A2 | 7/2009 |
| WO | WO-2009091922 A2 | 7/2009 |
| WO | WO-2009094463 A2 | 7/2009 |
| WO | WO-2009114479 A2 | 9/2009 |
| WO | WO-2011084477 A2 | 7/2011 |
| WO | WO-2015171814 A1 | 11/2015 |

OTHER PUBLICATIONS

Australia Exam Report for Application No. AU2006329867, Applicant: The Board of Trustees of Leland Stanford Junior University; dated Jan. 27, 2012, 2 pages.

Australia Exam Report for Application No. AU2007317886, Applicant: VertiFlex, Inc.; dated Jun. 18, 2012, 3 pages.

Australia Exam Report for Application No. AU2008241447, Applicant: VertiFlex, Inc.; dated Jul. 5, 2012, 4 pages.

(56) References Cited

OTHER PUBLICATIONS

Australia Exam Report for Application No. AU2008275708, Applicant: VertiFlex, Inc.; dated Nov. 12, 2012, 4 pages.
Australia Exam Report for Application No. AU2008279680, Applicant: VertiFlex, Inc.; dated Oct. 30, 2012, 5 pages.
Australia Exam Report for Application No. AU2008296066, Applicant: VertiFlex, Inc.; dated Mar. 6, 2013, 3 pages.
Australia Exam Report for Application No. AU2008343092, Applicant: VertiFlex, Inc.; dated Feb. 8, 2013, 4 pages.
Australia Exam Report for Application No. AU2013273815, Applicant: The Board of Trustees of Leland Stanford Junior University; dated Apr. 17, 2015, 3 pages.
Australia Exam Report for Application No. AU2014203394, Applicant: VertiFlex, Inc., dated Mar. 15, 2016, 2 pages.
Australia Exam Report No. 1 for Application No. AU2009206098, Applicant: VertiFlex, Inc.; dated Mar. 6, 2013, 4 pages.
Australia Exam Report No. 2 for Application No. AU2009206098, Applicant: VertiFlex, Inc.; dated Aug. 19, 2014, 4 pages.
Canada Exam Report for Application No. CA2634251, Applicant: The Board of Trustees of Leland Stanford Junior University; dated Dec. 3, 2013, 2 pages.
Canada Exam Report for Application No. CA2668833, Applicant: Vertiflex, Inc.; dated Dec. 5, 2013, 2 pages.
Canada Exam Report for Application No. CA2695937, Applicant: Vertiflex, Inc.; dated Aug. 7, 2014, 2 pages.
Canada Exam Report for Application No. CA2697628, Applicant: Vertiflex, Inc.; dated Oct. 16, 2014, 2 pages.
Canada Exam Report for Application No. CA2698718, Applicant: Vertiflex, Inc.; dated May 20, 2014, 3 pages.
Choi, Gun et al., "Percutaneous Endoscopic Interlaminar Disectomy for Intracanalicular Disc Herniations at L5-S1 Using a Rigid Working Channel Endoscope," Operative Neurosurg., 58: pp. 59-68 (2006).
European Examination Report for Application No. 08794704.0; Applicant: Vertiflex, Inc.; dated Apr. 5, 2017, 6 pages.
European Examination Report for Application No. 08799267.3; Applicant: Vertiflex, Inc.: dated Sep. 5, 2017, 4 pages.
European Further Exam Report for Application No. EP09702116.6; Applicant: VertiFlex, Inc.; dated Jul. 4, 2016, 4 pages.
Fast, Avital et al., "Surgical Treatment of Lumbar Spinal Stenosis in the Elderly," Arch Phys. Med Rehabil., Mar. 1985, pp. 149-151, vol. 66.
First Examination Report in European Patent Application No. 08780034.8, dated Jan. 16, 2017, 5 pages.
International Search Report and Written Opinion; Application No. PCT/US2006/047824; dated Oct. 16, 2008, 17 pages.
International Search Report and Written Opinion; Application No. PCT/US2006/048611; dated Oct. 14, 2008; 10 pages.
International Search Report and Written Opinion; Application No. PCT/US2006/048614; dated Feb. 3, 2006; 23 pages.
International Search Report and Written Opinion; Application No. PCT/US2007/022171; dated Apr. 15, 2008, 9 pages.
International Search Report and Written Opinion; Application No. PCT/US2007/023312; dated May 22, 2008, 14 pages.
International Search Report and Written Opinion; Application No. PCT/US2008/004901; dated Aug. 19, 2008, 7 pages.
International Search Report and Written Opinion; Application No. PCT/US2008/008382; dated Mar. 2, 2009, 13 pages.
International Search Report and Written Opinion; Application No. PCT/US2008/008983; dated Feb. 23, 2009, 7 pages.
International Search Report and Written Opinion; Application No. PCT/US2008/075487; dated Dec. 31, 2008, 7 pages.
International Search Report and Written Opinion; Application No. PCT/US2008/087527; dated Jul. 30, 2008, 10 pages.
International Search Report and Written Opinion; Application No. PCT/US2009/031150; dated Aug. 28, 2009, 6 pages.
Lee, Seungcheol et al., "New Surgical Techniques of Percutaneous Endoscopic Lumbar Disectomy for Migrated Disc Herniation," Joint Dis. Rel. Surg., 16(2); pp. 102-110 (2005).
Lee, Seungcheol et al., "Percutaneous Endoscopic Interlaminar Disectomy for L5-S1 Disc Herniation: Axillary Approach and Preliminary Results," J. of Korean Neurosurg. Soc., 40: pp. 19-83 (2006).
McCulloch, John A., Young, Paul H., "Essentials of Spinal Microsurgery," 1998, pp. 453-485. Lippincott-Raven Publishers, Philadelphia, PA (37 pages total).
Minns, R.J., et al., "Preliminary Design and Experimental Studies of a Noval Soft Implant for Correcting Sagittal Plane Instability in the Lumbar Spine," (1997) Spine, 22(16): 1819-1827.
Palmer, Sylvain et al., "Bilateral decompressive surgery in lumbar spinal stenosis associated with spondylolisthesis: unilateral approach and use of a microscope and tubular retractor system," Neurosurgery Focus, Jul. 2002, pp. 1-6, vol. 13.
Supplementary European Search Report for Application No. EP06845480; Applicant: VertiFlex, Inc.; Date of Completion: Aug. 14, 2012, 9 pages.
Supplementary European Search Report for Application No. EP07861426; Applicant: VertiFlex, Inc.; dated Jun. 7, 2011, 6 pages.
Supplementary European Search Report for Application No. EP07861721.4; Applicant: VertiFlex, Inc.; dated Nov. 24, 2009, 6 pages.
Supplementary European Search Report for Application No. EP08742949.4; Applicant: VertiFlex, Inc.; dated Sep. 17, 2012, 6 pages.
Supplementary European Search Report for Application No. EP08780034.8; Applicant: VertiFlex, Inc.; dated Sep. 19, 2012, 7 pages.
Supplementary European Search Report for Application No. EP08794704.0; Applicant: VertiFlex, Inc.; dated Oct. 23, 2012, 9 pages.
Supplementary European Search Report for Application No. EP08799267.3; Applicant: VertiFlex, Inc.; dated Jun. 29, 2011, 7 pages.
Supplementary European Search Report for Application No. EP08867282.9; Applicant: VertiFlex, Inc.; dated Nov. 28, 2012, 10 pages.
Supplementary European Search Report for Application No. EP09170304.1; Applicant: VertiFlex, Inc.; dated Nov. 24, 2009, 5 pages.
Supplementary European Search Report for Application No. EP09170338.9; Applicant: VertiFlex, Inc.; dated Nov. 24, 2009, 6 pages.
Supplementary European Search Report for Application No. EP09702116.6; Applicant: VertiFlex, Inc.; dated Feb. 11, 2011, 7 pages.
Supplementary European Search Report for Application No. EP11151901.3; Applicant: VertiFlex, Inc.; dated Apr. 7, 2011, 6 pages.
Supplementary European Search Report for Application No. EP13184922.6; Applicant: VertiFlex, Inc.; dated Oct. 30, 2013, 8 pages.
Supplementary European Search Report; Application No. EP07861426.0; Applicant: Vertiflex, Inc.; Date of Completion: Jun. 7, 2011, 6 pages.
Supplementary European Search Report; Application No. EP07861721.4; Applicant: Vertiflex, Inc.; Date of Completion: Nov. 24, 2009, 6 pages.
Supplementary European Search Report; Application No. EP09170304.1; Applicant: Vertiflex, Inc.; Date of Completion: Nov. 11, 2009, 5 pages.
Supplementary European Search Report; Application No. EP09170338.9; Applicant: Vertiflex, Inc.; Date of Completion: Nov. 12, 2009, 6 pages.
Supplementary European Search Report; Application No. EP09702116.6; Applicant: Vertiflex, Inc.; Date of Completion: Feb. 11, 2011, 6 pages.
Supplementary European Search Report; Application No. EP11151901.3; Applicant: Vertiflex, Inc.; Date of Completion: Apr. 7, 2011, 6 pages.
Swan, Colby, "Preliminary Design and Experimental Studies of a Novel Soft Implant for Correcting Sogittal Plane Instability in the Lumbar Spine," Spine, 1997, 22(16), 1826-1827.

(56) References Cited

OTHER PUBLICATIONS

Tredway, Trent L. et al., "Minimally Invasive Transforaminal Lumbar Interbody Fusion (MI-TLIF) and Lateral Mass Fusion with the MetRx System," (14 pages total), 2005.
Vaccaro, Alexander J. et al., MasterCases Spine Surgery, 2001, pp. 100-107. Thieme Medical Publishers, Inc., NY. (10 pages total).
Vertos mild Devices Kit—PRT-00430-C—Instructions for Use (13 pages total); see http://vertosmed.com/docs/mildIFU_PRT-00430-C.pdf., 2012.
Further Examination Report in European Patent Application No. 07861426.0, dated Oct. 4, 2017, 4 pages.
Further Examination Report in European Patent Application No. 08867282.9, dated Oct. 15, 2018, 7 pages.
U.S. Appl. No. 15/966,287 for Altarac et al., filed Apr. 30, 2018.
U.S. Appl. No. 16/054,917 for Kim, filed Aug. 3, 2018.
U.S. Appl. No. 16/116,696 for Altarac et al., filed Aug. 29, 2018.
U.S. Appl. No. 16/116,735 for Altarac et al., filed Aug. 29, 2018.
U.S. Appl. No. 16/046,806 for Altarac et al., filed Jul. 26, 2018.

* cited by examiner

SECTION A-A

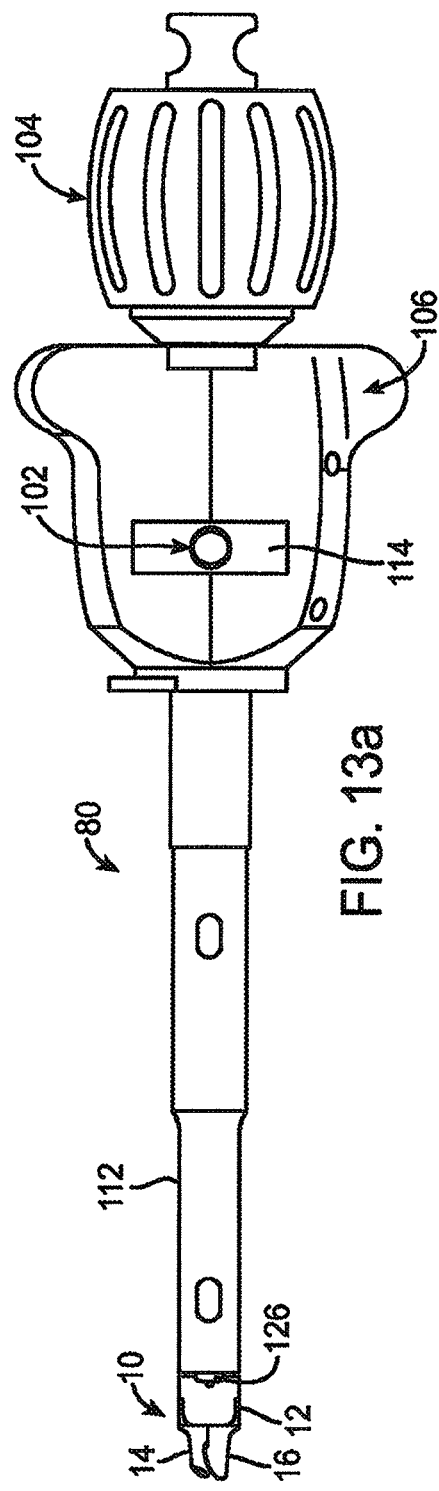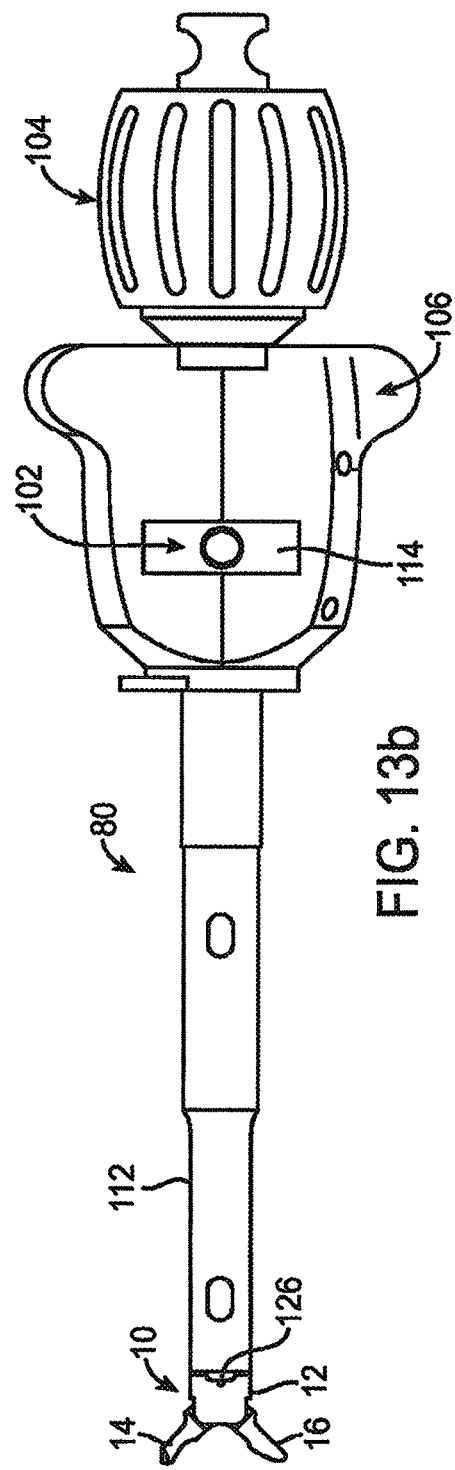
FIG. 13a
FIG. 13b

INTERSPINOUS SPACER

CROSS-REFERENCE TO RELATED APPLICATIONS

This application is a continuation of U.S. patent application Ser. No. 14/488,175, now U.S. Pat. No. 9,532,812, entitled Interspinous spacer" filed on Sep. 16, 2014, which is a continuation of U.S. patent application Ser. No. 12/354,517, now U.S. Pat. No. 8,864,828, entitled interspinous spacer" filed on Jan. 15, 2009, which claims priority to and the benefit of and is a continuation-in-part of U.S. Provisional Patent Application Ser. No. 61/011,199 entitled "Interspinous spacer" filed on Jan. 15, 2008, all of which [is] incorporated herein by reference in their entireties.

Mention is also made U.S. patent application Ser. No. 12/338,793, now U.S. Pat. No. 8,613,747, entitled "Spacer insertion instrument" filed on Dec. 18, 2008 which is a non-provisional of U.S. Provisional Patent Application Ser. No. 61/008,418 entitled "Spacer insertion instrument" filed on Dec. 19, 2007, all of which are incorporated herein by reference in their entireties.

Additional mention is made of U.S. patent application Ser. No. 12/205,511, now U.S. Pat. No. 8,123,782, entitled "Interspinous spacer" filed on Sep. 5, 2008 which is a nonprovisional of U.S. Provisional Patent Application Ser. No. 60/967,805 entitled "Interspinous spacer" filed on Sep. 7, 2007 and U.S. patent application Ser. No. 12/220,427, now U.S. Pat. No. 8,277,488, entitled "Interspinous spacer" filed on Jul. 24, 2008 which is a non-provisional of U.S. Provisional Patent Application Ser. No. 60/961,741 entitled "Interspinous spacer" filed on Jul. 24, 2007 and U.S. patent application Ser. No. 12/217,662, now U.S. Pat. No. 8,273,108, entitled "Interspinous spacer" filed on Jul. 8, 2008 which is a nonprovisional of U.S. Provisional Patent Application No. 60/958,876 entitled "Interspinous spacer" filed on Jul. 9, 2007 and U.S. patent application Ser. No. 12/148,104, now U.S. Pat. No. 8,292,922, entitled "Interspinous spacer" filed on Apr. 16, 2008 which is a non-provisional of U.S. Provisional Patent Application Ser. No. 60/923,971 entitled "Interspinous spacer" filed on Apr. 17, 2007 and U.S. Provisional Patent Application Ser. No. 60/923,841 entitled "Spacer insertion instrument" filed on Apr. 16, 2007, all of which are hereby incorporated by reference in their entireties.

Further mention is made of U.S. patent application Ser. No. 11/593,995, now U.S. Pat. No. 8,425,559, entitled "Systems and methods for posterior dynamic stabilization of the spine" filed on Nov. 7, 2006 and U.S. patent application Ser. No. 11/582,874, now U.S. Pat. No. 8,128,662, entitled "Minimally invasive tooling for delivery of interspinous spacer" filed on Oct. 18, 2006 and U.S. patent application Ser. No. 11/314,712, now U.S. Pat. No. 8,152,837, entitled "Systems and methods for posterior dynamic stabilization of the spine" filed on Dec. 20, 2005 and U.S. patent application Ser. No. 11/190,496, now U.S. Pat. No. 8,409,282 entitled "Systems and methods for posterior dynamic stabilization of the spine" filed on Jul. 26, 2005 and U.S. patent application Ser. No. 11/079,006, now U.S. Pat. No. 8,012,207, entitled "Systems and methods for posterior dynamic stabilization of the spine" filed on Mar. 10, 2005 which is a continuation-in-part of U.S. patent application Ser. No. 11/052,002, now U.S. Pat. No. 8,317,864, entitled "Systems and methods for posterior dynamic stabilization of the spine" filed on Feb. 4, 2005 which is a continuation-in-part of U.S. patent application Ser. No. 11/006,502, now U.S. Pat. No. 8,123,807, entitled "Systems and methods for posterior dynamic stabilization of the spine" filed on Dec. 6, 2004 which is a continuation-in-part of U.S. patent application Ser. No. 10/970,843, now U.S. Pat. No. 8,167,944, entitled "Systems and methods for posterior dynamic stabilization of the spine" filed on Oct. 20, 2004.

All of the above-mentioned applications and patents are hereby incorporated by reference in their entireties.

BACKGROUND

With spinal stenosis, the spinal canal narrows and pinches the spinal cord and nerves, causing pain in the back and legs. Typically, with age, a person's ligaments may thicken, intervertebral discs may deteriorate and facet joints may break down—all contributing to the condition of the spine characterized by a narrowing of the spinal canal. Injury, heredity, arthritis, changes in blood flow and other causes may also contribute to spinal stenosis.

Doctors have been at the forefront with various treatments of the spine including medications, surgical techniques and implantable devices that alleviate and substantially reduce debilitating pain associated with the back. In one surgical technique, a spacer is implanted between adjacent spinous processes of a patient's spine. The implanted spacer opens the foramen and spinal canal, maintains the desired distance between vertebral body segments, and as a result, avoids impingement of nerves and relieves pain. For suitable candidates, an implantable interspinous spacer may provide significant benefits in terms of pain relief. However, there is a need for an implantable interpsinous spacer for patients with adjacent spinous processes that are not aligned such as in patients suffering with scoliosis. Scoliosis is the lateral or sideways curvature caused by congenital, neuromuscular, idiopathic, syndromic or postural conditions. An example of a scoliotic spine is shown in FIG. 12.

Any surgery is an ordeal. However, the type of device and how it is implanted has an impact. For example, one consideration when performing surgery to implant an interspinous spacer is the size of the incision that is required to allow introduction of the device. Small incisions and minimally invasive techniques are quick and generally preferred as they affect less tissue and result in speedier recovery times. As such, there is a need for interspinous spacers that work well with surgical techniques that are minimally invasive for a patient with misaligned spinous processes such as patients with scoliosis. The present invention sets forth such a spacer.

SUMMARY

According to one aspect of the invention, an implant configured for placement between adjacent spinous processes in a spinal motion segment with a scoliotic curve and configured to laterally stabilize the spacer with respect to said adjacent spinous processes is provided.

An implant for placement between adjacent spinous processes in a spinal motion segment is provided. The implant includes a body defining a longitudinal passageway through at least a portion of the body. A first arm connected to the body and capable of rotation with respect to the body. The first arm has a first pair of extensions and a first bridge defining a spinous process receiving portion for seating a first spinous process therein. The first arm has a first proximal canting surface. The implant further includes a second arm connected to the body and capable of rotation with respect to the body. The second arm has a second pair of extensions and a second bridge defining a spinous process receiving portion for seating a second spinous process therein. The second arm has a second proximal earning surface. The implant further includes an actuator connected to the body. The actuator is configured such that the actuator is disposed inside the body and configured to move relative to the body and contact the earning surfaces of the arms to rotate them from a first configuration in which the arms are substantially parallel to the longitudinal axis of the body to a second configuration in which the first arm seats the first spinous process and the second arm seats the second spinous process. At least one of the first arm and second aim is configured to seat the spinous processes of a spinal motion segment with a scoliotic curve.

An implant for placement between adjacent spinous processes in a spinal motion segment is provided. The implant includes a body defining a longitudinal axis. A first arm is connected to the body and has a first pair of extensions defining a spinous process receiving portion for seating a superior spinous process therein. The implant includes a second arm connected to the body. The second arm has a second pair of extensions defining a spinous process receiving portion for seating an inferior spinous process therein. One extension of the first pair and one extension of the second pair that are adjacent to each other on the same side of the spacer are both shorter than the other of the extensions.

An implant for placement between adjacent spinous processes in a spinal motion segment is provided. The implant includes a body defining a longitudinal axis. A first arm is connected to the body having a first pair of extensions defining a spinous process receiving portion for seating a superior spinous process therein. A second aim is connected to the body. The second arm has a second pair of extensions defining a spinous process receiving portion for seating an inferior spinous process therein. The distance between the first pair of extensions is greater than the distance between the second pair of extensions to accommodate a generally wider lower or caudal end of a superior spinous process relative to a generally narrower upper or cephalad end of an inferior spinous process.

An implant for placement between adjacent spinous processes in a spinal motion segment is provided. The implant includes a body defining a longitudinal axis. A first arm is connected to the body and configured to laterally stabilize the body with respect to a first spinous process when in a deployed configuration. A second arm is connected to the body and configured to laterally stabilize the body with respect to a second spinous process when in a deployed configuration. The first and second arms are configured for placement between adjacent spinous processes in which at least one of the adjacent spinous processes has a projection in a coronal plane that is angled with respect to the sagittal plane.

BRIEF DESCRIPTION OF THE DRAWINGS

FIG. 13a is a side view of a spacer connected to an insertion instrument according to the present invention.

FIG. 13b is a side view of a spacer in a partially deployed configuration connected to an insertion instrument according to the present invention.

DETAILED DESCRIPTION

Figure 1A:
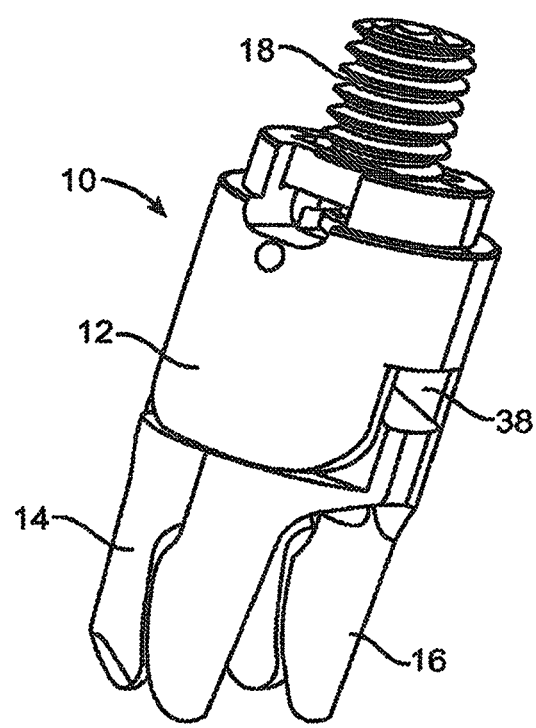
FIG. 1a is a perspective view of a spacer according to the present invention.
Figure 1B:
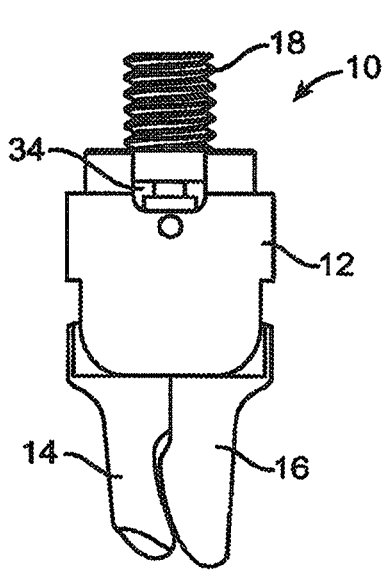
FIG. 1b is a side view of a spacer according to the present invention.

With reference to FIGS. 1a-1f, various views of a spacer 10 according to the present invention are shown. The spacer 10 includes a body 12, a superior extension member, arm or wing 14, an inferior extension member, arm or wing 16, and an actuator assembly 18.

Turning now to FIGS. 2a-2d, the body will now be described. The body 12 is shown to have a clamshell construction with a left body piece 20 (shown in FIGS. 2a and 2b) joined to a right body piece 22 (shown in FIGS. 2c and 2d) to capture arms 14, 16 inside. With the right and left body pieces 20, 22 joined together, the body 12 is generally cylindrical. The spacer body 12 has a cross-sectional size and shape that allows for implantation between adjacent spinous processes and facilitates delivery into a patient through a narrow port or cannula.

The inside of the body 12 defines an arm receiving portion 24 and an actuator assembly receiving portion 26 with features formed in each of the left and right body pieces 20, 22 that together define the arm and actuator assembly receiving portions 24, 26. In one variation, the arm receiving portion 24 includes slots 28 that receive pins formed on the arms 14, 16 such that the pins rotate and/or translate inside the slots 28. The actuator assembly receiving portion 26 includes a threaded passageway 30. Other features include a tongue and groove for mating with the opposite clamshell.

Figure 1C:
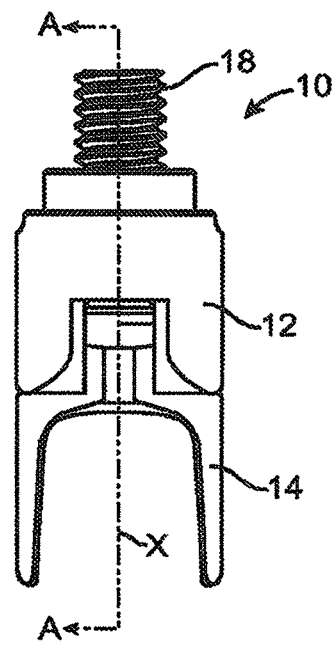
FIG. 1c is a top view of a spacer according to the present invention.
Figure 1D:
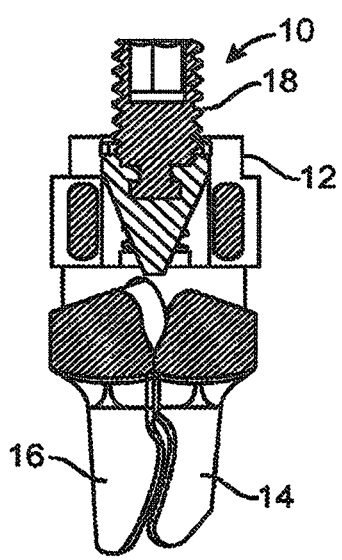
FIG. 1d is a cross-sectional view of a spacer taken along line A-A of FIG. 1c according to the present invention.
Figure 1E:
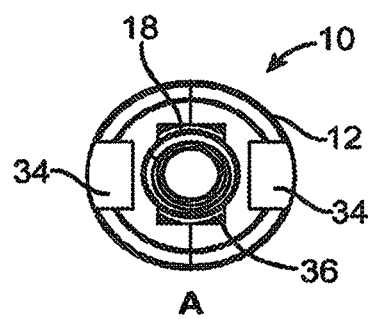
FIG. 1e is an end view of a spacer according to the present invention.
Figure 1F:
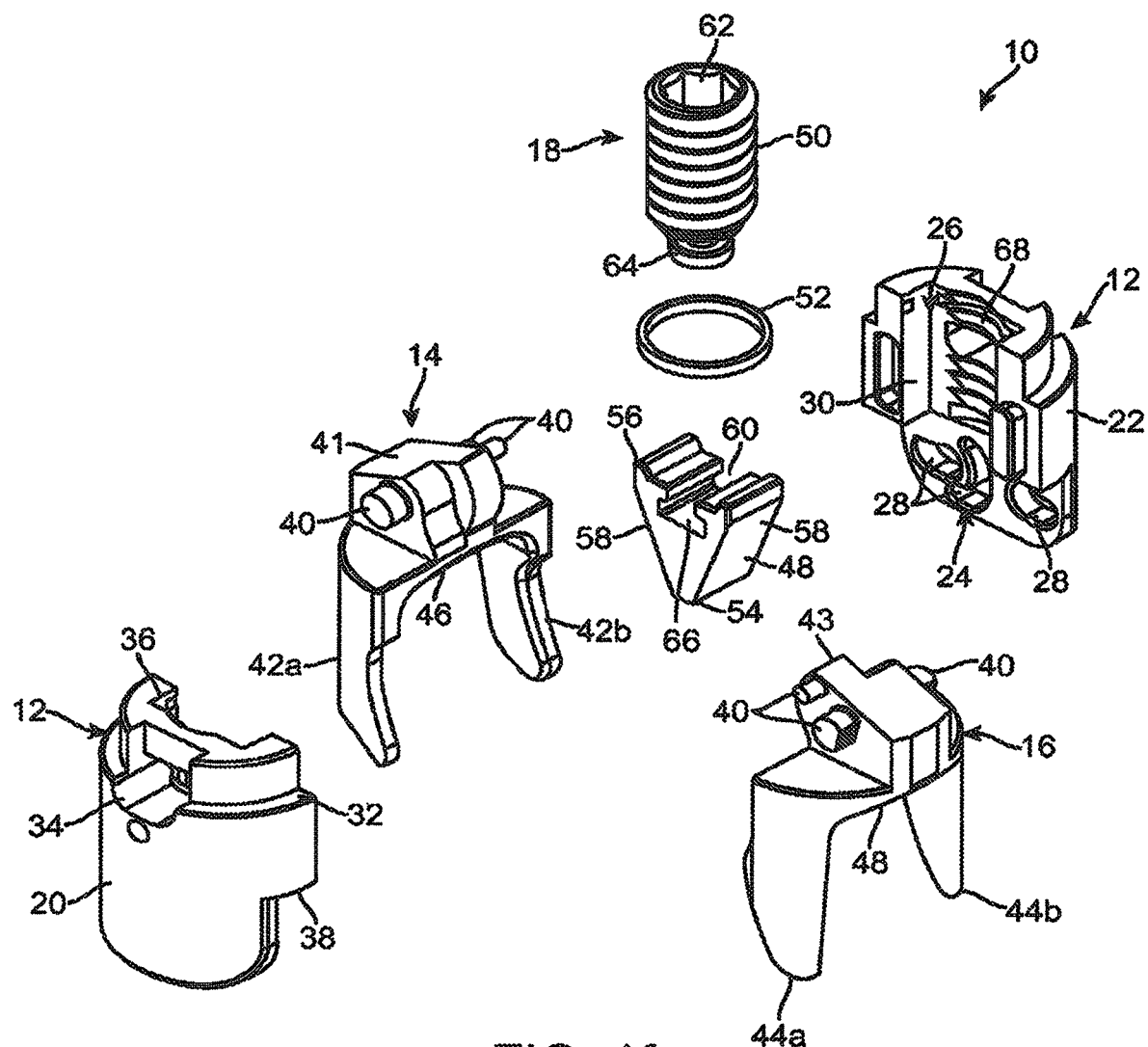
FIG. 1f is an exploded view of a spacer according to the present invention.
Figure 2A:
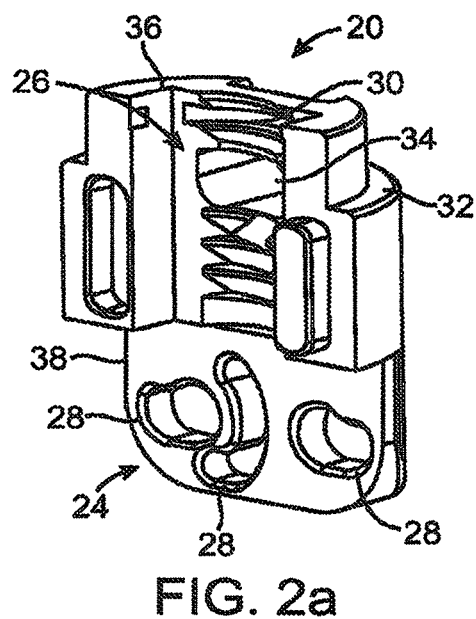
FIG. 2a is a perspective view of a half of a body of a spacer according to the present invention.
Figure 2B:
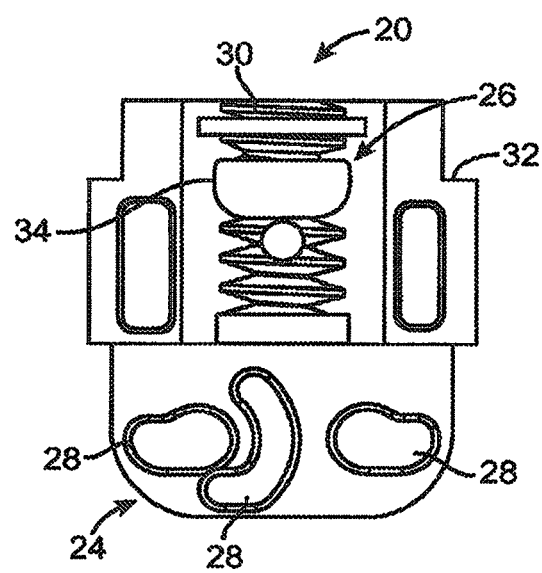
FIG. 2b is a side view of half of a body of a spacer according to the present invention.
Figure 2C:
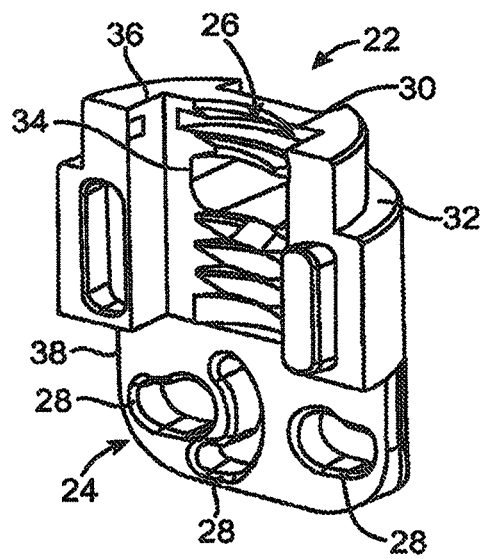
FIG. 2c is a perspective view of a half of a body of a spacer according to the present invention.
Figure 2D:
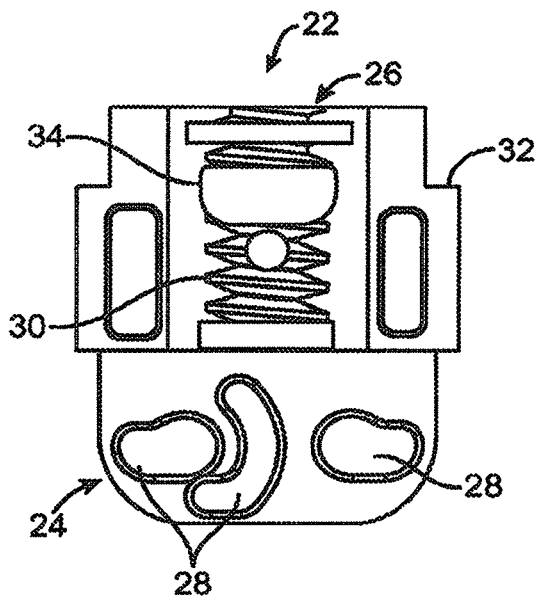
FIG. 2d is a side view of half of a body of a spacer according to the present invention.

The outside of the body 12 defines a ledge 32 along at least a portion of the periphery. Notches 34 are formed at opposite locations and are configured for pronged attachment to a spacer delivery instrument. When joined together, the left and right body pieces 20, 22 define a proximal opening 36 (as also seen in FIG. 1e) and a distal opening 38 (as also seen in FIG. 1a) in the body 12. A longitudinal scallop (not shown) extending from the proximal end of the spacer to the distal end is formed to facilitate placement of the spacer 10 between and to conform to the anatomy of adjacent spinous processes. In one variation, two oppositely located longitudinal scallops are formed in the outer surface of the body 12 such that, when implanted in a patient's spine, one scallop faces the superior spinous process and the other scallop faces the inferior spinous process. In one variation, the distance between oppositely located longitudinal scallops is approximately 8.0 millimeters imparting the spacer 10 with a low profile advantageous for insertion between closely spaced or "kissing" spinous processes.

Figure 3A:
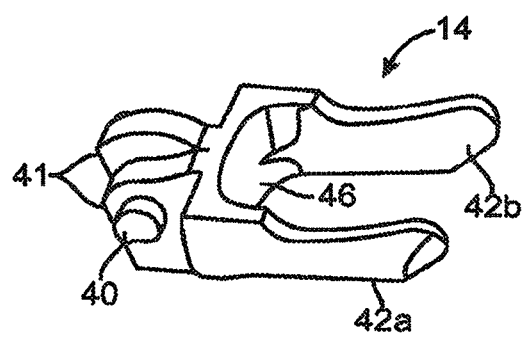
FIG. 3a is a perspective view of a superior wing of a spacer according to the present invention.
Figure 3B:
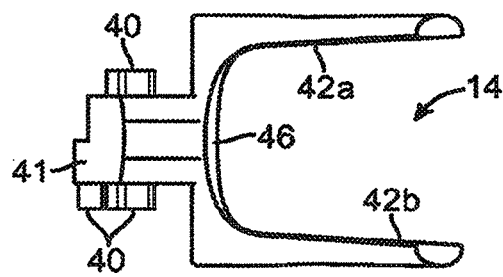
FIG. 3b is a top view of a superior wing of a spacer according to the present invention.
Figure 3C:
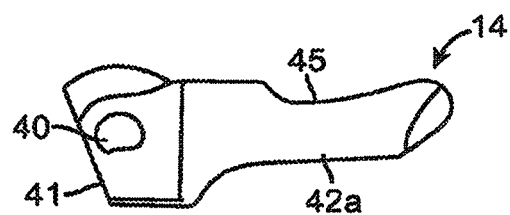
FIG. 3c is a side view of a superior wing of a spacer according to the present invention.
Figure 3D:
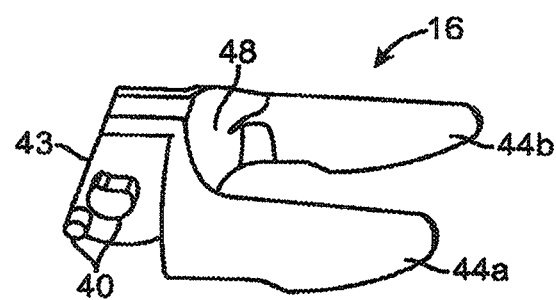
FIG. 3d is a perspective view of an inferior wing of a spacer according to the present invention.
Figure 3E:
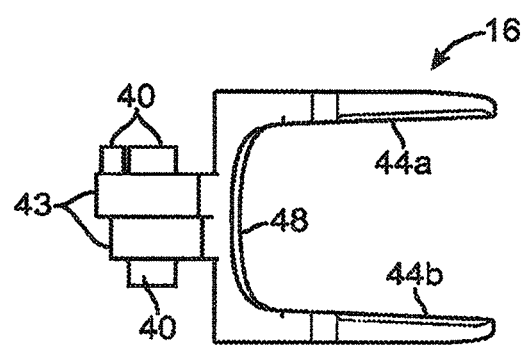
FIG. 3e is a bottom view of an inferior wing of a spacer according to the present invention.
Figure 3F:
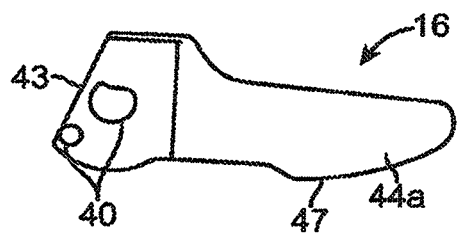
FIG. 3f is a side view of an inferior wing of a spacer according to the present invention.

Turning now to FIGS. 3a-3c, the superior arm 14 is shown and in FIGS. 3d-3f, the inferior arm 16 is shown. The superior and inferior aims 14, 16 include pins 40 for mating with the body 12, in particular, for mating with the slots 28 of the arm receiving portion 24. Each of the superior and inferior aims 14, 16 includes at least one earning surface 41, 43, respectively, for contact with the actuator assembly 18. The superior and inferior arms 14, 16 include elongated superior extensions 42a, 42b and elongated inferior extensions 44a, 44b, respectively. Extensions 42a and 44a are located on the left adjacent to the left body piece 20 and extensions 42b and 44b are located on right adjacent to the right body piece 22. Superior extensions 42a, 42b extend substantially parallel to each other in both an undeployed configuration and in a fully-deployed configuration as do inferior extensions 44a, 44b. Extending between extensions 42a, 42b is a strut, bridge, bracket or saddle 46 that forms a superior substantially U-shaped configuration that is sized and configured to receive a superior spinous process. As seen in FIG. 3c, the anterior face of the superior extensions 14 includes a slight concavity or curvature 45 for conforming to the bony anatomy of the superior spinous process and or lamina. Extending between inferior extensions 44a, 44b is a strut, bridge, bracket or saddle 48 that forms an inferior substantially U-shaped configuration that is sized and configured to receive an inferior spinous process of a spinal motion segment. As seen in FIG. 3f, the anterior face of the inferior extensions 16 includes a slight convexity or curvature 47 for conforming to the bony anatomy of the inferior spinous process and/or lamina. In one variation, the length of the saddle 46 of the superior arm 14 is approximately 9.0 millimeters and the length of the saddle 48 of the inferior arm 16 is approximately 7.0 millimeters. Also, the tip-to-tip distance of the superior extensions 42a, 42b is approximately 10.0 millimeters and the tip-to-tip distance of the inferior extensions 44a, 44b is approximately 9.0 millimeters. In sum, the seat comprising the saddle 46 and superior extensions 42a, 42b formed by the superior arm 14 is larger than the seat comprising the saddle 48 and inferior extensions 44a, 44b formed by the inferior arm 16. The larger superior seat of the spacer conforms closely to a wider lower end of the spinous process and the smaller inferior seat of the spacer conforms closely to a narrower upper end of the adjacent inferior spinous process when the spacer 10 is inserted between adjacent spinous processes as spinous processes are naturally narrower on top and wider on the bottom and thereby providing greater lateral stability to the spacer with respect to the spinous processes.

Figure 4A:
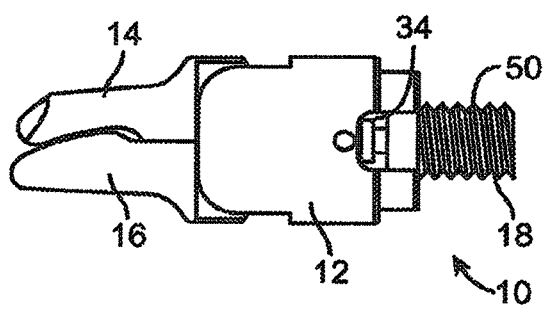
FIG. 4a is a side view of a spacer according to the present invention.
Figure 4B:
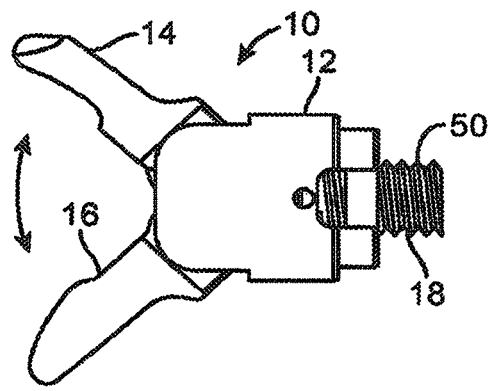
FIG. 4b is a side view of a spacer with wings partially deployed according to the present invention.
Figure 4C:
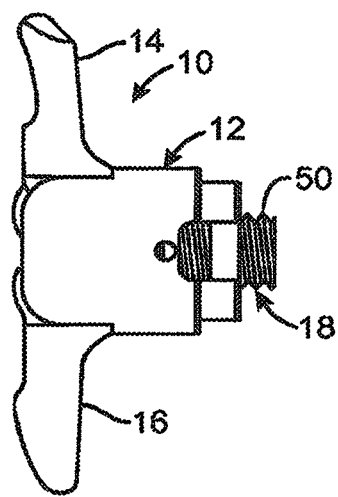
FIG. 4c is a side view of a spacer with wings in a deployed configuration according to the present invention.
Figure 4D:
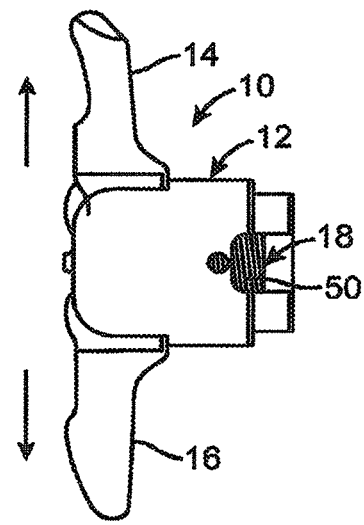
FIG. 4d is a side view of a spacer with wings in a deployed and extended configuration according to the present invention.
Figure 5C:
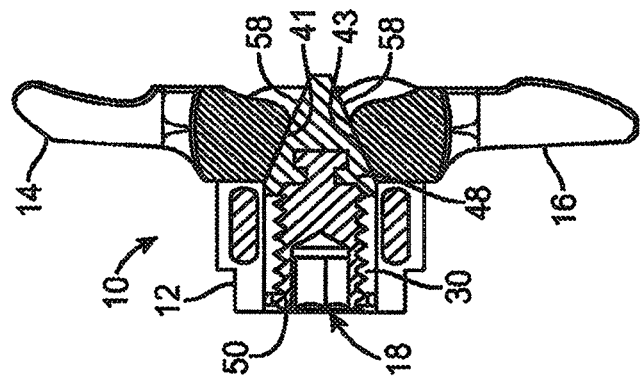
FIG. 5c is a cross-sectional view of a spacer with wings in a deployed and extended configuration according to the present invention.

The superior and inferior arms 14, 16 are movably or rotatably connected to the body 12, for example by hinge means or the like to provide rotational movement from an undeployed configuration to a deployed configuration that arcs through about a 90 degree range or more with respect to the body 12. The arms 14, 16 are rotationally movable between at least an undeployed, collapsed or folded state (as shown in FIGS. 1a-1e) and at least a fully deployed state (as shown in FIGS. 4c, 5c and 6c). In the undeployed state, the arm pairs 14, 16 are aligned generally or substantially axially (i.e., axially with the longitudinal axis defined by the body 12 or to the translation path into the interspinous space of the patient) to provide a minimal lateral or radial profile. The longitudinal axis X of the spacer 10 and body 12 is shown in FIG. 1c. In the deployed state, the arm pairs 14, 16 are positioned generally or substantially transverse to the collapsed position (i.e., transverse to the longitudinal axis defined by the body 12 or to the translation path into the interspinous space of the patient). In the deployed state, the arm pairs 14, 16 are positioned such that each of the U-shaped saddles are in a plane (or individual planes) or have a substantially U-shaped projection in a plane that is generally or substantially transverse to the longitudinal axis X defined by the body 12 or to the collapsed position or to the implantation path into the interspinous space of the patient. In one variation, the spacer 10 is configured such that the arms 14, 16 are linearly moveable or translatable within the same transverse plane from the deployed state (such as the state shown in FIGS. 4c, 5b and 6b) to and from an additionally extended state or second deployed state (such as the state shown in FIGS. 4d, 5c and 6c) characterized by an additional translation of at least one of the arms 14, 16 with respect to the body 12 along the direction of the arrows in FIGS. 4d and 6c away from or towards the body 12. More specifically, the arms 14, 16 can be extended in the general vertical or lateral direction along an axis along the general length of the spine wherein the arms 14, 16 are extended away from each other and away from the body 12 as denoted by the arrows in FIG. 4d. The arms 14, 16 can be un-extended in a direction towards each other and towards the body 12 for un-deployment or repositioning of the spacer 10 and shown by the arrows in FIG. 6c. This extended feature advantageously allows for the most minimally invasive configuration for the spacer without compromising the ability of the spacer 10 to seat and contain the spinous processes or to laterally stabilize the spacer relative to the spinous processes in between levels where the anatomy of the spinous processes is such that the interspinous process space increases in the anterior direction of the patient or without compromising the ability of the spacer to provide adequate distraction. The arms 14, 16 are connected to the body 12 and/or to each other in a manner that enables them to be moved simultaneously or independently of each other, as well as in a manner that provides passive deployment and/or vertical extension or, alternatively, active or actuated deployment and/or vertical extension.

Turning back to FIG. 1f, the actuator assembly 18 will now be described. The actuator assembly 18 includes an actuator 48, shaft 50 and retainer 52. The actuator 48 includes a distal end 54 and a proximal end 56 and at least two bearing surfaces 58. The bearing surfaces 58 angle towards each other from the proximal end 56 to the distal end 54. The proximal end 56 of the actuator 48 includes a shaft receiving portion 60 configured to receive the shaft 50. In one variation, the shaft 50 is integrally formed with the actuator 48. The distal end 54 of the actuator 48 is further configured to engage the superior and inferior arms 14, 16 such that forward translation of the actuator 48 relative to the body 12 effects deployment of the arms into at least one deployed configuration. The actuator assembly 18 is at least partially disposed inside the body 12 and is configured to move with respect to the body 12.

Still referencing FIG. 1, the shaft 50 is substantially cylindrical in shape and includes a threaded outer surface for engagement with the threaded inner surface of the actuator assembly receiving portion 26 of the body 12. The threads on the inner surface of the body 12 are formed by the conjunction of both left and right body pieces 20, 22. The proximal end of the shaft 50 includes a hex socket 62 for receiving a driving tool. The distal end of the shaft 50 includes an actuator engagement portion 64 configured to connect to the actuator 48. The actuator engagement portion 64 as shown in FIG. 1 is a projection that slides into a channel 66 on the actuator 48. Once inserted into the channel 66, movement of the shaft 50 solely along the longitudinal axis of the spacer 10 will not release the shaft 50 from the actuator 48.

Still referencing FIG. 1, the retainer 52 is a circular ring preferably made of metal such as steel or titanium. The retainer 52 fits into a recess 68 formed on the inner surface of the body 12. When pressed into the recess 68, the retainer 52 secures the actuator 48 inside the passageway 30 of the body 12.

Assembly of the spacer 10 with reference to FIGS. 1a-1f will now be described. The arms 14, 16 are disposed in the arm receiving portion 24 of one body piece. The other of the left or right body piece 20, 22 is securely connected/welded to the one body piece thereby capturing the arms 14, 16 inside the arm receiving portion 24 such that the arms 14, 16 are capable of at least rotational movement with respect to the body 12 and in one variation, capable of rotational movement and translation with respect to the body 12. The shaft 50 is connected to the actuator 48 and together inserted and threadingly connected into the passageway 30 of the body 12. The retainer 52 is passed over the proximal end of the shall 50 and snapped into the recess 68 of the body 12 to secure the actuator assembly 18 inside the body 12 such that the actuator assembly 18 is capable of threaded translational movement with respect to the body 12.

To deliver and deploy the spacer 10 within the patient, the spacer 10 is releasably attached to a delivery instrument (not shown) at the proximal end of the spacer 10 via notches 34. The spacer 10 is provided or otherwise placed in its undeployed state as illustrated in FIG. 4a. In the undeployed state and attached to a delivery instrument, the spacer 10 is inserted into a port or cannula which has been operatively positioned in an interspinous space within a patient's back and the outside of the patient via a minimally invasive incision. In some circumstances it may not be necessary to use a cannula where the device is inserted through a larger opening in the skin. Where a cannula is employed, the spacer 10 is then advanced through the cannula to within the targeted interspinous space between two adjacent spinous processes. The spacer 10 is advanced beyond the end of the cannula or, alternatively, the cannula is pulled proximately to uncover the spacer 10 within. A driver such as a hex-shaped tool is inserted into the hex socket 62 of the spacer 10 and turned to advance the shaft 50 of the actuator assembly 18. As the shaft 50 advances within the passageway 30, the bearing surfaces 58 of the actuator 48 contact the superior and inferior earning surfaces 41, 43 of the superior and inferior arms 14, 16 forcing the arms 14, 16 to rotate about their pins 40 with respect to the body 12. The arms 14, 16 rotate through an arc of approximately 90 degrees into the deployed configuration in which the superior and inferior extensions 42a, 42b, 44a, 44b are substantially perpendicular to the longitudinal axis of the spacer 10 as shown in FIGS. 4c and 4d. In one variation, continued advancement of the actuator assembly 18 forces the arms 14, 16 outwardly in the direction of the arrows in FIG. 4d. Such outward translation is guided by the length and shape of the slots 28. Once deployed, the superior arm 14 seats the superior spinous process and the inferior arm 16 seats the adjacent inferior spinous process.

Retelling now to FIGS. 4a-4d, the spacer 10 is shown in a closed, undeployed configuration (FIG. 4a), a partially deployed configuration or otherwise intermediary configuration (FIG. 4b), a deployed configuration (FIG. 4c) and a deployed and extended configuration (FIG. 4d). In FIGS. 4a-4d, the sagittal plane of the spacer 10 corresponds to the plane of the paper that bisects the spacer 10. In moving from an undeployed to a deployed configuration, the actuator assembly 18 and, in particular, the shaft 50 of the actuator assembly moves distally with respect to the body to a position flush or almost flush with the proximal end of the body 12 or to a position completely inside the body 12 disappearing from sight providing a low profile for the spacer 10 along the longitudinal axis of the body 12.

Figure 5B:
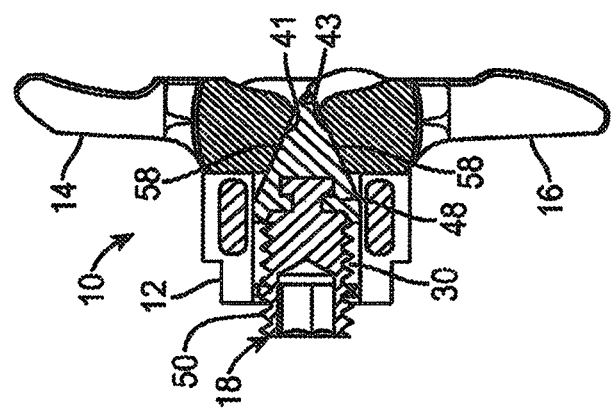
FIG. 5b is a cross-sectional view of a spacer with wings in a deployed configuration according to the present invention.
Figure 5A:
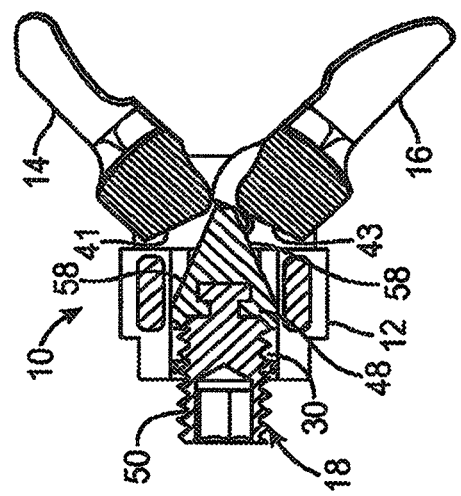
FIG. 5a is a cross-sectional view of a spacer with wings in a partially deployed configuration according to the present invention.

Turning now to the cross-sectional views of the spacer 10 in FIGS. 5a-5c, as the shaft 50 advances within the passageway 30, the bearing surfaces 58 of the actuator 48 contact the superior and inferior earning surfaces 41, 43 of the superior and inferior arms 14, 16 turning the arms 14, 16 into rotation with respect to the body 12. Upon rotation, the bearing surfaces 58 of the actuator 48 slide with respect to the superior and inferior caming surfaces 41, 43 of the superior and inferior arms 14, 16. The arms 14, 16 rotate through an arc of approximately 90 degrees with respect to the body 12 into the deployed configuration (FIG. 5b) in which the superior and inferior extensions of the arms 14, 16 are substantially perpendicular to the longitudinal axis of the spacer 10 as shown in FIG. 5b and with further actuation into a deployed and extended configuration as shown in FIG. 5c in which the arms 14, 16 have extended outwardly away from the body 12. The arms 14, 16 have a substantially U-shaped projection in a plane perpendicular to the longitudinal axis of the spacer 10 or a substantially U-shaped projection in a plane perpendicular to the longitudinal axis of the spacer 10.

Figure 6A:
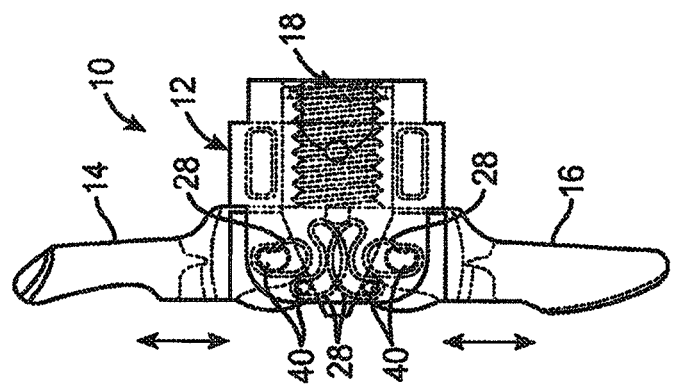
FIG. 6a is a semi-transparent view of a spacer with wings partially deployed according to the present invention.
Figure 6B:
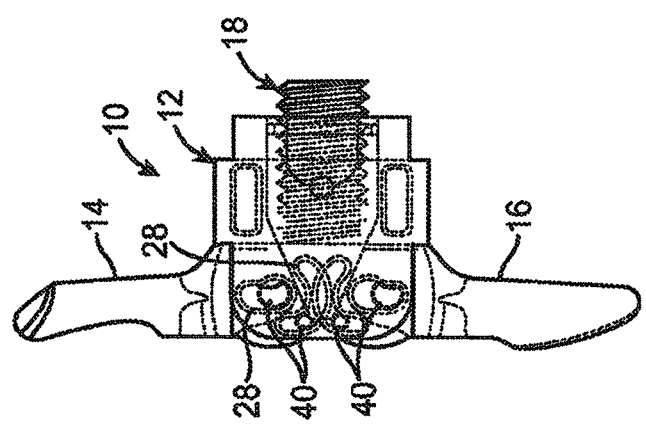
FIG. 6b is a semi-transparent view of a spacer with wings in a deployed configuration according to the present invention.
Figure 6C:
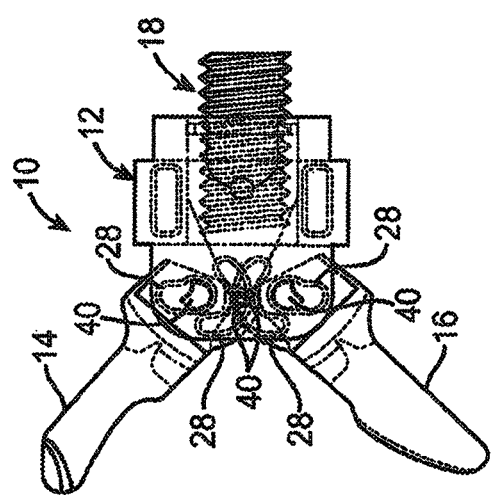
FIG. 6c is a semi-transparent view of a spacer with wings in a deployed and extended configuration according to the present invention.

Turning now to the semi-transparent views of the spacer 10 in FIGS. 6a-6c, the rotation of the pins 40 of the arms 14, 16 in the openings 28 of the body 12 is shown in moving from the configuration of FIG. 6a to the configuration of FIG. 6c. The translation of the pins 40 of the arms 14, 16 in the elongated portion of the slots 28 of the body 12 is shown in moving from the deployed configuration of FIG. 6b to the deployed and extended configuration of FIG. 6c in the direction of the arrows in FIG. 6c. Such outward translation with respect to the body 12 is guided by the length and shape of the slots 28. Reverse rotation of the spindle 86 moves the shaft 50 proximally with respect to the body 12 allowing the arms to close to any intermediary configuration between a deployed, configuration and an undeployed, closed configuration. This feature advantageously permits the surgeon to deploy and undeploy the spacer as needed to ease installation and positioning of the spacer with respect to patient anatomy.

Any of the spacers disclosed herein are configured for implantation employing minimally invasive techniques including through a small percutaneous incision and through the supraspinous ligament. Implantation through the supraspinous ligament involves selective dissection of the supraspinous ligament in which the fibers of the ligament are cut, separated or spread apart from each other in a manner to maintain as much of the ligament intact as possible such as cutting, separating or spreading in a direction parallel to the orientation of the ligament fibers. This approach avoids crosswise dissection or cutting of the ligament and thereby reduces the healing time and minimizes the amount of instability to the affected spinal segment. While this approach is ideally suited to be performed through a posterior or midline incision, the approach may also be performed through one or more incisions made laterally of the spine with or without affect to the supraspinous ligament. Of course, the spacer may also be implanted in a lateral approach that circumvents the supraspinous ligament altogether.

Other variations and features of the various mechanical spacers are covered by the present invention. For example, a spacer may include only a single arm which is configured to receive either the superior spinous process or the inferior spinous process or laterally stabilize the body of the spacer with respect to the superior spinous process and/or with respect to the inferior spinous process. The surface of the spacer body opposite the side of the single arm may be contoured or otherwise configured to engage the opposing spinous process wherein the spacer is sized to be securely positioned in the interspinous space and provide the desired distraction of the spinous processes defining such space. The additional extension of the arm(s) subsequent to their initial deployment in order to seat or to effect the desired distraction between the vertebrae may be accomplished by expanding the body portion of the device instead of or in addition to extending the individual extension members 14, 16.

The extension arms of the subject device may be configured to be selectively movable subsequent to implantation, either to a fixed position prior to closure of the access site or otherwise enabled or allowed to move in response to normal spinal motion exerted on the device after deployment. The deployment angles of the extension arms may range from less than 90 degrees (relative to the longitudinal axis defined by the device body) or may extend beyond 90 degrees. Each extension member may be rotationally movable within a range that is different from that of the other extension members. Additionally, the individual superior and/or inferior extensions 42a, 42b, 44a, 44b may be movable in any direction relative to the strut or bridge extending between an arm pair or relative to the device body in order to provide shock absorption and/or function as a motion limiter, or serve as a lateral adjustment particularly during lateral bending and axial rotation of the spine. The manner of attachment or affixation of the extensions to the arms may be selected so as to provide movement of the extensions that is passive or active or both. In one variation, the saddle or distance between extensions 42a and 42b or between 44a and 44b can be made wider to assist in seating the spinous process and then narrowed to secure the spinous process positioned between extensions 42a and 42b or between 44a and 44b. Spacers having different arm 14, 16 configurations will now be discussed.

Turning now to FIGS. 7-11, there is shown another variation of the spacer 10 according to the present invention wherein like numerals are used to describe like parts. The spacer 10 of FIGS. 7-11 is adapted for implantation into patients with adjacent spinous processes that are misaligned such as patients with scoliosis where the spine curves laterally forming an S-shaped or C-shaped curve. With reference to FIG. 12, there is shown a scoliotic spine. Cobb's angle is a measurement used for evaluation of curves in scoliosis on an anterior-posterior projection of the spine as shown in FIG. 12. When assessing a curve of the spine, the apical vertebra is first identified. The apical vertebra is the most likely displaced and rotated vertebra with the least tilted end plate. The end/transitional vertebra are then identified through the curve above and below. The end vertebrae are the most superior and inferior vertebrae which are least displaced and rotated and have the maximally tilted end plate. As shown in FIG. 12, a line is drawn along the superior end plate of the superior end vertebra and a second line drawn along the inferior end plate of the inferior end vertebra. If the end plates are indistinct the line may be drawn through the pedicles. The angle between these two lines (or lines drawn perpendicular to them) is measured as the Cobb angle. In S-shaped scoliosis where there are two contiguous curves the lower end vertebra of the upper curve will represent the upper end vertebra of the lower curve. Because the Cobb angle reflects curvature only in a single plane and fails to account for vertebral rotation it may not accurately demonstrate the severity of three dimensional spinal deformity. Generally, a Cobb angle of 10 is regarded as a minimum angulation to define scoliosis. In a normal spine the spinous processes of the spine are substantially aligned and lie in one plane, which for practical purposes will be defined as a sagittal plane. In particular, the projection of the spinous processes on a coronal plane will be substantially aligned with the sagittal plane. In a scoliotic spine, the spinous processes are angle with respect to the sagittal plane. In particular, the anterior-posterior projection of the spinous processes on a coronal plane will show at least one spinous process angled with respect to the sagittal plane.

Figure 7:
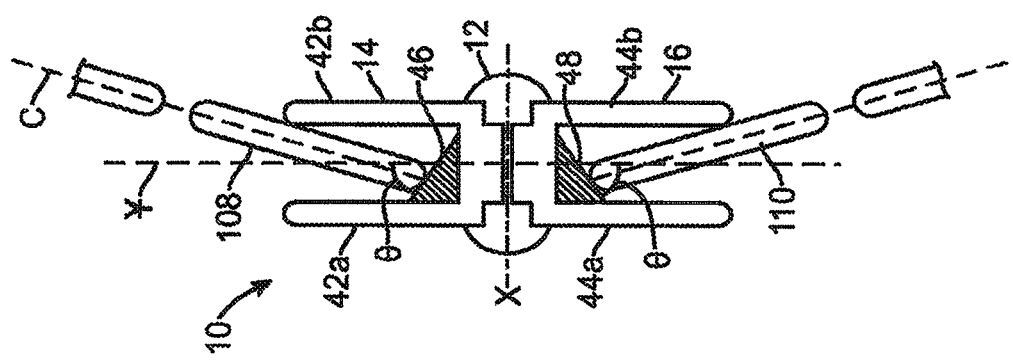
FIG. 7 is a partial cross-sectional view of a spacer according to the present invention located between two adjacent spinous processes.

FIG. 7 shows an anterior-posterior view of a partially cross-sectioned superior spinous process 108 and an adjacent inferior spinous process 110 between which the spacer 10 is implanted in a portion of a spine showing a scoliotic curve C convex to the left. The spacer 10 of FIG. 7 includes superior and inferior arms 14, 16 adapted to a scoliotic curve C that is convex to the left. The remaining components of the spacer 10 such as the body 12 and actuator assembly 18 are similar if not identical to the same components described above with respect to FIGS. 1-6.

The superior and inferior arms 14, 16 include elongated superior extensions 42a, 42b and elongated inferior extensions 44a, 44b respectively. Extensions 42a and 44a are located on the left and extensions 42b and 44b are located on the right. Superior extensions 42a, 42b extend substantially parallel to each other in both an undeployed configuration and fully deployed configuration as do inferior extensions 44a, 44b. As shown, extensions 42a, 42b, 44a, 44b are substantially parallel to the Y axis.

Extending between superior extensions 42a, 42b is a strut, bridge, bracket or saddle 46 that, together with superior extensions 42a, 42b, form a superior receiving portion or seat that is sized and configured to laterally stabilize the body 12 with respect to the superior spinous process 108 and in one variation configured to receive at least a portion of a superior spinous process 108. In previous embodiments described above, when in the fully deployed configuration, the bridge 46 is substantially perpendicular to the superior extensions 42a, 42b and substantially parallel to the X-Z plane where Z corresponds to the longitudinal axis of the spacer 10 extending into and out of the page. In the embodiment shown in FIG. 7, the bridge 46 is angled with respect to the superior extensions 42a, 42b to adapt to the convex left scoliotic curve C. The angled bridge 46 is integrally formed with the superior arm 14 or alternatively, the bridge 46 is a wedge-shaped insert adapted to modify a spacer 10 into a spacer 10 having an angled bridge 46. The plane of the bridge 46 in the transverse or X-Y plane forms an angle θ with the Y-Z plane that is between 0 and 90 degrees, preferably between 5 and 60 degrees.

The Y-Z plane, where Z corresponds to the longitudinal axis of the spacer 10 extending into and out of the page, is the sagittal plane of the spacer 10 and it may or may not correspond to the sagittal plane of the patient's body or spine. FIG. 7 shows the superior spinous process 108 and inferior spinous process 110 angled with respect to the sagittal plane with extensions 42 and 44 being substantially parallel to the sagittal plane.

Extending between inferior extensions 44a, 44b is a strut, bridge, bracket or saddle 48 that, together with inferior extensions 44a, 441s, form an inferior receiving portion that is sized and configured to laterally stabilize the body 12 with respect to the inferior spinous process 110 and in one variation configured to receive at least a portion of an adjacent inferior spinous process 110. In previous embodiments described above, when in the fully deployed configuration, the bridge 48 is substantially perpendicular to the inferior extensions 44a, 44b and substantially parallel to the X-Z plane where Z corresponds to the longitudinal axis of the spacer 10 extending into and out of the page. In the embodiment shown in FIG. 7, the bridge 48 is angled with respect to the inferior extensions 44a, 44b or angle with respect to the sagittal plane to adapt to the convex left scoliotic curve C. The angled bridge 48 is integrally formed with the inferior arm 16 or alternatively, the bridge 48 is a wedge-shaped insert adapted to modify a spacer 10 into a spacer 10 having an angled bridge 48. The plane of the bridge 48 in the transverse or X-Y plane forms an angle θ with the Y-Z plane or sagittal plane that is between 0 and 90 degrees, preferably between 5 and 60 degrees.

As shown in FIG. 7, the angled bridges 46, 48 conform the spacer 10 to the scoliotic curve such that the superior and inferior spinous processes 108, 110 are seated in the superior and inferior arms 14, 16, or receiving portion of those arms, respectively, when in the deployed configuration. In another variation, the right superior extension 42b is slightly shorter in length relative to the left superior extension 42a to better accommodate the angled superior spinous process in a convex left scoliotic curve as shown in FIG. 7. Also, the right inferior extension 44b is slightly shorter in length relative to the left inferior extension 44a to better accommodate the angled inferior spinous process in the convex left scoliotic curve. Furthermore, only one of the bridges 46, 48 need be angled.

Figure 8:
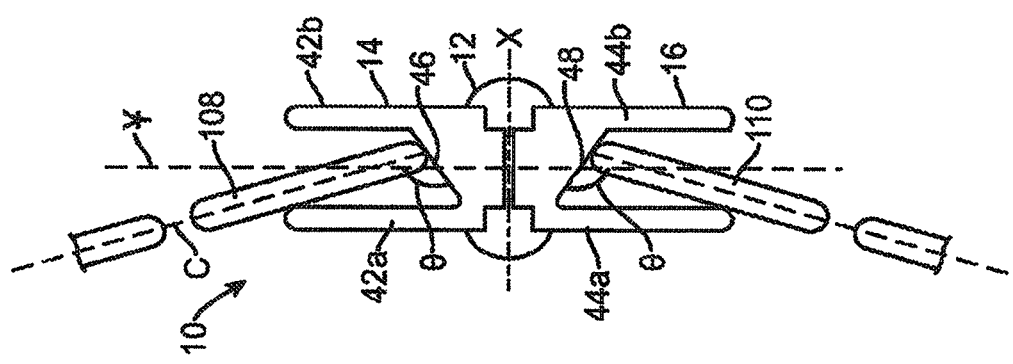
FIG. 8 is a cross-sectional, view of a spacer according to the present invention located between two adjacent spinous processes.

Turning now to FIG. 8, there is shown another variation of the spacer 10 according to the present invention wherein like numerals are used to describe like parts. The spacer 10 of FIG. 8 is adapted for implantation into patients with adjacent spinous processes that are misaligned such as patients with scoliosis where the spine curves laterally forming an S-shaped or C-shaped curve. FIG. 8 shows a superior spinous process 108 and an adjacent inferior spinous process 110 between which the spacer 10 is implanted in a portion of a spine showing a scoliotic curve C convex to the right. The spacer 10 of FIG. 8 includes superior and inferior arms 14, 16 configured to a scoliotic curve C that is convex to the right. The remaining components of the spacer 10 such as the body 12 and actuator assembly 18 of the spacer 10 are similar if not identical to the same components described above with respect to FIGS. 1-6.

The superior and inferior arms 14, 16 include elongated superior extensions 42a, 42b and elongated inferior extensions 44a, 44b, respectively. Extensions 42a and 44a are located on the left and extensions 42b and 44b are located on the right. Superior extensions 42a, 42b extend substantially parallel to each other in both an undeployed configuration and fully deployed configuration as do inferior extensions 44a, 44b.

Still referencing FIG. 8, extending between superior extensions 42a, 42b is a strut, bridge, bracket or saddle 46 that, together with superior extensions 42a, 42b, form a superior receiving portion that is sized and configured to laterally stabilize the body 12 with respect to the superior spinous process 108 and in one variation receive a superior spinous process 108. As shown, extensions 42a, 42b, 44a, 44b are substantially parallel to the Y-Z plane. In previous embodiments described above, the bridge 46 is substantially perpendicular to the superior extensions 42a, 42b and substantially parallel to the X-Z plane where Z corresponds to the longitudinal axis of the spacer 10 extending into and out of the page. In the embodiment shown in FIG. 8 the bridge 46 is angled with respect to the superior extensions 42a, 42b to adapt to the convex right scoliotic curve C. The angled bridge 46 is integrally formed with the superior arm 14 or alternatively, the bridge 46 is a wedge-shaped insert adapted to modify a spacer 10 into a spacer 10 having an angled bridge 46. The plane of the bridge 46 in the transverse or X-Y plane forms an angle θ with the Y-Z plane or sagittal plane that is between 90 and 180 degrees, preferably between 120 and 175 degrees.

Extending between inferior extensions 44a, 44b is a strut, bridge, bracket or saddle 48 that, together with inferior extensions 44a, 44b, form an inferior receiving portion that is sized and configured to laterally stabilize the body 12 with respect to the inferior spinous process 110 and in one variation to receive an adjacent inferior spinous process 110. In previous embodiments described above, the bridge 48 is substantially perpendicular to the inferior extensions 44a, 44b and substantially parallel to the X-Z plane where Z corresponds to the longitudinal axis of the spacer 10 extending into and out of the page. In the embodiment shown in FIG. 8, the bridge 48 is angled with respect to the inferior extensions 44a, 44b to adapt the spacer 10 to the convex right scoliotic curve C. The angled bridge 48 is integrally formed with the inferior arm 16 or alternatively, the bridge 48 is a wedge-shaped insert adapted to modify a spacer 10 into a spacer 10 having an angled bridge 48. The plane of the bridge 48 in the transverse or X-Y plane forms an angle θ with the Y-Z plane that is between 90 and 180 degrees, preferably between 120 and 175 degrees.

As shown in FIG. 8, the angled bridges 46, 48 conform to the scoliotic curve such that the superior and inferior spinous processes 108, 110 are seated in the superior and inferior arms 14, 16, respectively, when in the deployed configuration. In another variation, the left superior extension 42a is slightly shorter in length relative to the right superior extension 42b to better accommodate the angled superior spinous process in a convex right scoliotic curve as shown in FIG. 8. Also, the left inferior extension 44a is slightly shorter in length relative to the right inferior extension 44b to better accommodate the angled inferior spinous process in a convex right scoliotic curve.

Figure 9:
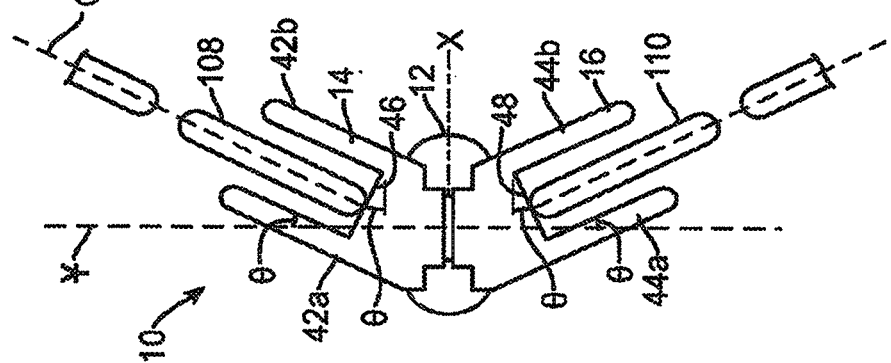
FIG. 9 is a cross-sectional view of a spacer according to the present invention located between two adjacent spinous processes.

Turning now to FIG. 9, there is shown another variation of the spacer 10 according to the present invention wherein like numerals are used to describe like parts. The spacer 10 of FIG. 9 is adapted for implantation into patients with adjacent spinous processes that are misaligned such as patients with scoliosis where the spine curves laterally forming an S-shaped or C-shaped curve. FIG. 9 shows a superior spinous process 108 and an adjacent inferior spinous process 110 between which the spacer 10 is implanted in a portion of a spine showing a scoliotic curve C convex to the left. The spacer 10 of FIG. 9 includes superior and inferior arms 14, 16 adapted to a scoliotic curve C that is convex to the left in which the superior and inferior arms 14, 15 are angled. The spacer 10 may also be configured with superior and inferior arms 14, 16 adapted to a scoliotic curve C that is convex to the right in which the superior and inferior arms, 14, 15 are angled in the opposite direction. The remaining components such of the spacer 10 as the body 12 and actuator assembly 18 of the spacer 10 are similar if not identical to the same components described above with respect to FIGS. 1-6.

Still referencing FIG. 9, the superior and inferior arms 14, 16 include elongated superior extensions 42a, 42b and elongated inferior extensions 44a, 44b respectively. Extensions 42a and 44a are located on the left and extensions 42b and 44b are located on the right. Superior extensions 42a, 42b extend substantially parallel to each other in both an undeployed configuration and fully deployed configuration as do inferior extensions 44a, 44b.

In the variation of FIG. 9, the superior extensions 42a, 42b are angled such that the superior extensions 42a, 42b form an angle θ with respect to the Y-Z plane or sagittal plane when in the deployed configuration where Z corresponds to the longitudinal axis of the spacer 10 extending into and out of the page. The angle θ is between 0 and 90 degrees, preferably between 5 and 75 degrees. Likewise, inferior extensions 44a, 44b are also angled such that the inferior extensions 44a, 44b form an angle θ with the Y-Z plane when in the deployed configuration. The angle θ is between 0 and 90 degrees, preferably between 5 and 75 degrees. The superior arm 14 extensions 42a, 42b need not have the same angle θ as the inferior arm 16 extensions 44a, 44b.

Still referencing FIG. 9, extending between superior extensions 42a, 42b is a strut, bridge, bracket or saddle 46 that, together with superior extensions 42a, 42b, form a superior receiving portion that is sized and configured laterally stabilize the body 12 with respect to the superior spinous process 108 and in one variation to receive a superior spinous process 108. The bridge 46 is substantially perpendicular to the superior extensions 42a, 42b. In the embodiment shown in FIG. 10, the plane of the bridge 46 in the X-Y plane is angled with respect to the X-Z plane or sagittal plane by the angle θ that is between 0 and 90 degrees, preferably between 5 and 75 degrees to adapt to the scoliotic curve convex to the left.

Extending between inferior extensions 44a, 44b is a strut, bridge, bracket or saddle 48 that, together with inferior extensions 44a, 44b, form an inferior receiving portion that is sized and configured to laterally stabilize the body 12 with respect to the inferior spinous process 110 and in one variation to receive an adjacent inferior spinous process 110. The bridge 48 is substantially perpendicular to the inferior extensions 44a, 44b. In the embodiment shown in FIG. 9, the plane of the bridge 48 in the X-Y plane is angled with respect to the X-Z plane by an angle θ that is between 0 and 90 degrees, preferably between 5 and 75 degrees to adapt to the scoliotic curve convex to the left. As shown in FIG. 9, the angled bridges 46, 48 conform to the scoliotic curve such that the superior and inferior spinous processes 108, 110 are received in the superior and inferior arms 14, 16, respectively, when in the deployed configuration.

Figure 10:
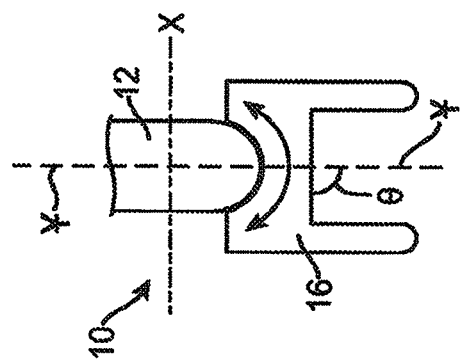
FIG. 10 is a partial view of a spacer according to the present invention.
Figure 11:
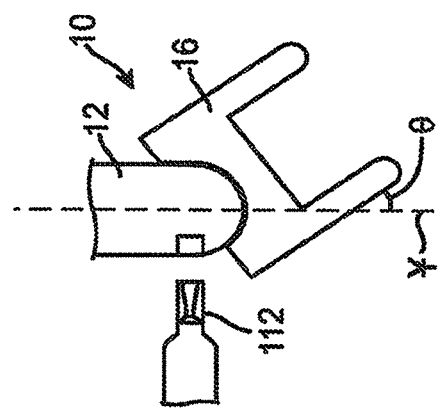
FIG. 11 is a partial view of a spacer and driving tool according to the present invention.
Figure 12:
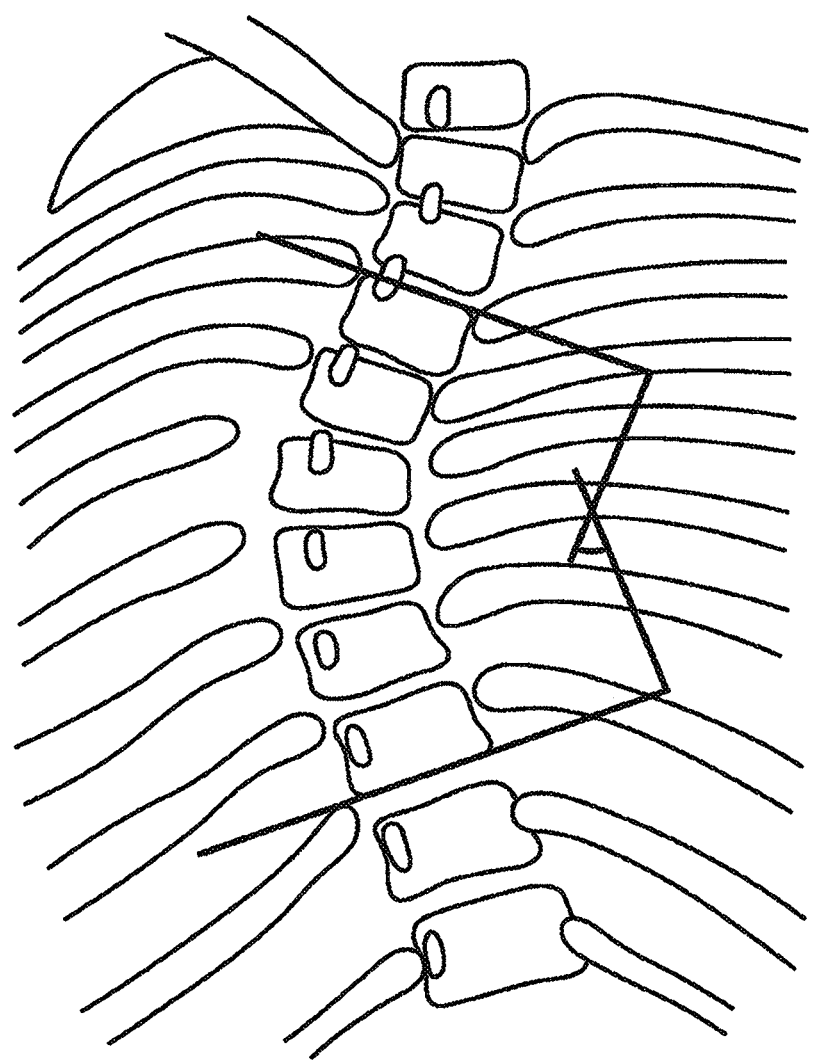
FIG. 12 is a posterior view of part of a spine with a scoliotic curve.

Turning now to FIGS. 10 and 11, there is shown a partial anterior-posterior view of a spacer 10 illustrating a portion of the body 12 and an inferior arm 16. The spacer 10 of FIG. 10 includes at least one arm that articulates in the direction of the arrows to accommodate a convex right or convex left scoliotic curve of varying degrees. Only the inferior arm is shown in FIGS. 10 and 11. The angle θ that the bridge 48 in the X-Y plane makes with respect to the Y-Z plane or sagittal plane where Z corresponds to the longitudinal axis of the spacer 10 extending into and out of the page is adjusted and locked by a driving tool 112 shown in FIG. 11 and configured to angulate the superior arm 14 and/or inferior arm 16 as desired so that the superior arm 14 seats the superior spinous 108 process and the inferior arm 16 seats the inferior spinous process 110.

The spacer 10 of FIGS. 7-11 are delivered and deployed within the patient in the same manner as described above with respect to FIGS. 1-6. The spacers 10 of FIGS. 9-11 that are angled before delivery into the patient require the clinician to angle the spacer 10 during delivery into the interspinous space. For example, when in the undeployed configuration, spacer 10 of FIG. 9 or the spacer 10 of FIGS. 10 and 11 that is angled before delivery, requires insertion first along a path parallel to the superior and inferior extensions 42a, 42b, 44a, 44b. The spacer 10 is then turned such that the body 12 trailing the extensions is oriented parallel to the same path so that the extensions conform to the scoliotic curvature. Otherwise, the delivery and deployment of the spacer 10 proceeds as described herein.

The spacer 10 is provided or otherwise placed in its undeployed, closed state in juxtaposition to the insertion instrument 80 and connected thereto as shown in FIG. 13a. The longitudinal axis of the insertion instrument 80 is advantageously aligned with the longitudinal axis of the spacer 10 as shown. The delivery instrument 80 includes a first subassembly 102 to releasably clamp to the body 12 of the spacer 10 at a distal end of the insertion instrument 80. The first subassembly 102 includes an inner clamp shaft (not shown) having flexible prongs 126 at the distal end configured for attachment to the body 12 of the spacer 10 and, in particular, for insertion into the notches 34 of the spacer body 12. The first subassembly 102 includes an outer shaft 112 located over the inner clamp shaft and configured for relative motion with respect to one another via a control 114 located at the handle assembly 106. The control 114 is threaded to the outer shaft 112 such that rotation of the control 114 moves the outer shaft 112 along the longitudinal axis of the insertion instrument 80 over the inner clamp shaft to deflect and undeflect the prongs 126 to connect or disconnect the instrument 80 to or from the body 12. The first control 114 is activated at the handle of the insertion instrument 80 such that the first subassembly 102 is connected to the body 12 of the spacer 10. The first control 114 is rotated in one direction to advance the outer shaft 112 over the inner clamp shaft (not shown) deflecting the prongs 126 inwardly into the notches 34 on the body 12 of the spacer 10 to secure the spacer body 12 to the instrument as shown in FIG. 13a. Reverse rotation of the control 114 reverses the direction of translation of the outer shaft 112 to release the prongs 126 from the notches 34 and, thereby, release the spacer 10 from the instrument 80.

Still referencing FIG. 13a, the insertion instrument 80 includes a second subassembly 104 that is configured to connect to the actuator assembly 18 of the spacer 10. In particular, the second subassembly 104 includes means located at the distal end of the second subassembly 104 to activate the actuator assembly 18. In one variation, the second subassembly 104 is a pronged driver having an elongated shaft that is configured to be insertable into the notches of a spindle. In another variation, the second subassembly 104 is an elongated shaft with hexagonally-shaped tip configured to be insertable into a corresponding hexagonally shaped socket 62 of the shaft 50. The second subassembly 104 is insertable at the proximal end of the instrument 80 and extends through the handle assembly 106 and through the inner. The removable driver 104 is rotatable with respect to the instrument 80 to rotate the shaft 50 and arrange the spacer 10 to and from deployed and undeployed configurations.

Figure 13C:
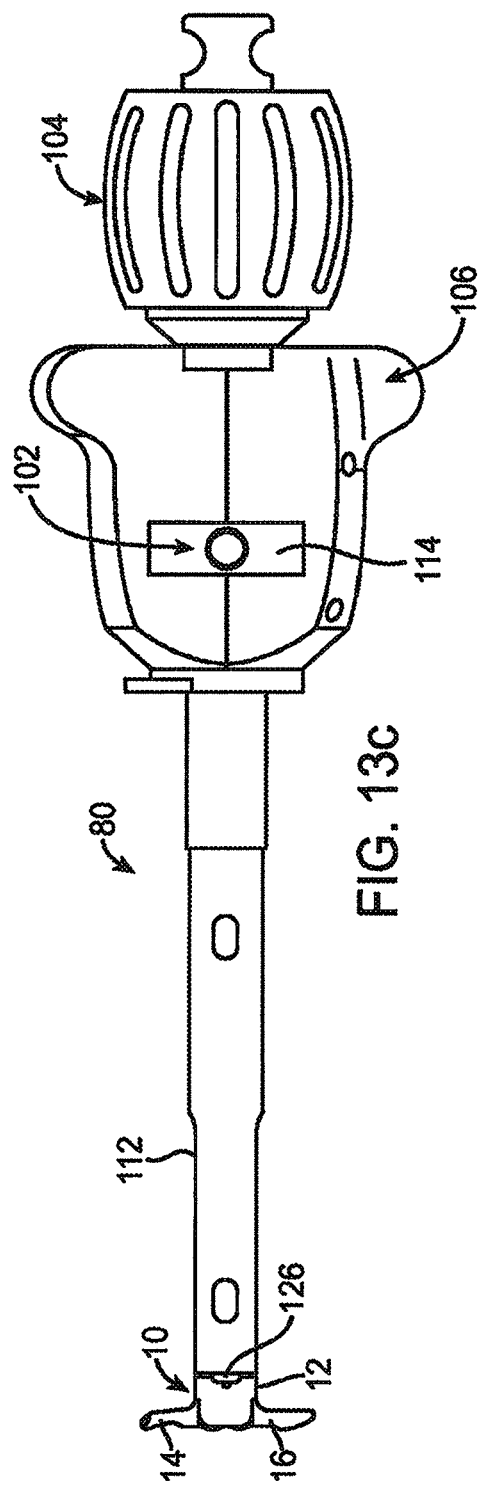
FIG. 13c is a side view of a spacer in a deployed configuration connected to an insertion instrument according to the present invention.

To deliver and deploy the spacer 10 within the patient, the spacer 10 is releasably attached to a delivery instrument 80 at the proximal end of the spacer 10 as shown in FIG. 13a. A small midline or lateral-to-midline incision is made in the patient for minimally-invasive percutaneous delivery. In one variation, the supraspinous ligament is avoided. In another variation, the supraspinous ligament is split longitudinally along the direction of the tissue fibers to create an opening for the instrument. Dilators may be further employed to create the opening. In the undeployed state with the arms 14, 16 in a closed orientation and attached to a delivery instrument 80, the spacer 10 is inserted into a port or cannula, if one is employed, which has been operatively positioned to an interspinous space within a patient's back and the spacer is passed through the cannula to the interspinous space between two adjacent vertebral bodies. The spacer 10 is advanced beyond the end of the cannula or, alternatively, the cannula is pulled proximately to uncover the spacer 10 connected to the instrument 80. Once in position, the second assembly 104 is inserted into the instrument 80 if not previously inserted to engage the actuator and is rotated to rotate the shaft 50. The rotating shaft 50 advances the actuator 48 to begin deployment the spacer 10. Rotation in one direction, clockwise, for example, threadingly advances the shaft 50 which then results in the actuator 48 contacting the superior and inferior canting surfaces 41, 43 of the superior and inferior arms 14, 16 to begin their deployment. FIG. 13b illustrates the superior arm 14 and the inferior arm 16 in a partially deployed position with the arms 14, 16 rotated away from the longitudinal axis. The position of the arms 14, 16 in FIG. 13b may be considered to be one of many partially deployed configurations or intermediary configurations that are possible and from which the deployment of the arms 14, 16 is reversible with opposite rotation of the second assembly 104. With further advancement, the arms 14, 16 rotate through an arc of approximately 90 degrees into the deployed configuration in which the superior and inferior extensions are substantially perpendicular to the longitudinal axis of the spacer 10 as shown in FIG. 13c.

Turning to FIG. 13c, there is shown an insertion instrument 80 connected to a spacer 10 in a first deployed configuration in which the arms 14, 16 are approximately 90 degrees perpendicular to the longitudinal axis or perpendicular to the initial undeployed configuration. Continued rotation of second assembly 104 rotates the shaft 50 further distally with respect to the body 12 of the spacer 10 pushing the bearing surfaces 58 further against the superior and inferior camming surfaces 41, 43. While in the first deployed configuration of FIG. 13c, the clinician can observe with fluoroscopy the positioning of the spacer 10 inside the patient and then choose to reposition the spacer 10 if desired. Repositioning of the spacer 10 may involve undeploying the arms 14, 16 by rotating the shaft 50 via the second assembly 104 to rotate the arms into any one of the many undeployed configurations and then moving the delivery instrument while connected to the spacer into a new position. The spacer wings may then be re-deployed into the desired location. This process can be repeated as necessary with or without undeployment of the wings until the clinician has achieved the desired positioning of the spacer in the patient. Of course, inspection of the spacer 10 may be made via fluoroscopy while the spacer 10 is in an intermediate or partially deployed configuration such as that of FIG. 13b.

Figure 13D:
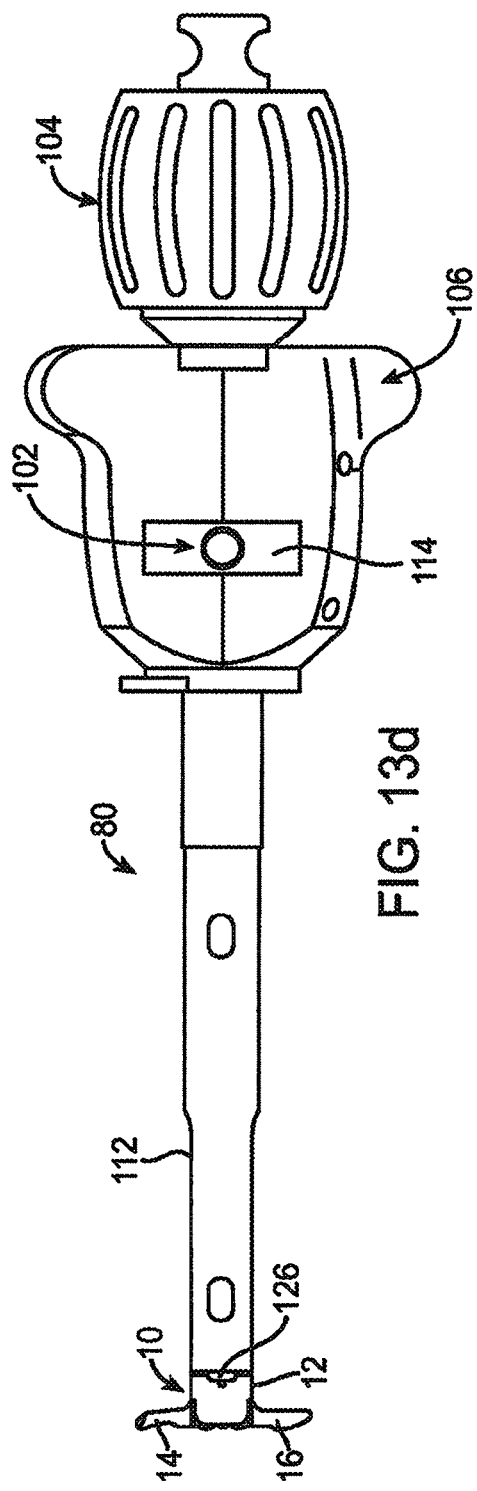
FIG. 13d is a side view of a spacer in a deployed and extended configuration connected to an insertion instrument according to the present invention.

Even further advancement of the actuator shaft 50 via rotation of the second subassembly 104 from the first deployed configuration results in the spacer 10 assuming a second deployed configuration shown in FIG. 13d, if the spacer 10 is so configured as to allow a second deployed configuration. The second deployed configuration is an extended configuration as described above in which the superior and inferior arms 14, 16 extend transversely with respect to the longitudinal axis outwardly in the direction of the arrows in FIG. 4d. The spacer 10 is configured such that the outward translation of the arms 14, 16 follows the rotation into 90 degrees and is guided by the length and shape of the openings 28 in which the arms 14, 16 move. Once deployed, the superior arm 14 seats the superior spinous process and the inferior arm 16 seats the adjacent inferior spinous process. Such extension may also provide some distraction of the vertebral bodies.

Figure 14:
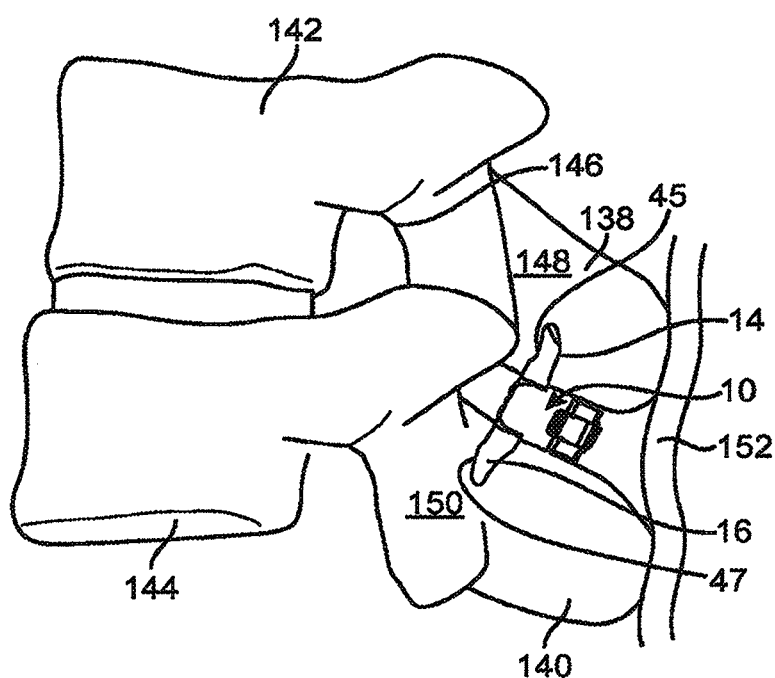
FIG. 14 is a perspective view of a spacer in a deployed configuration according to the present invention implanted between adjacent spinous processes of two vertebral bodies.

Following deployment, the second assembly 104 may be removed. Control 114 is rotated in the opposite direction to release the body 12 from the instrument 80. The insertion instrument 80, thus released from the spacer 10, is removed from the patient leaving the spacer 10 implanted in the interspinous process space as shown in FIG. 14. In FIG. 14, the spacer 10 is shown with the superior arm 14 seating the superior spinous process 138 of a first vertebral body 142 and the inferior arm 16 seating the inferior spinous process 140 of an adjacent second vertebral body 144 providing sufficient distraction to open the neural foramen 146 to relieve pain. As mentioned above, the shape of the superior arm 14 is such that a superior concavity or curvature 45 is provided to conform to the widening of the superior spinous process 138 in an anterior direction of the patient toward the superior lamina 148 going in the anterior direction. In general, the superior arm 14 is shaped to conform to anatomy in the location in which it is seated. Likewise, as mentioned above, the shape of the inferior arm 16 is such that an inferior convexity or curvature 47 is provided to conform to the widening of the inferior spinous process 140 in an anterior direction toward the inferior lamina 150. The supraspinous ligament 152 is also shown in FIG. 14. In FIG. 14, the lateral direction is into and out of the page and the superior 14 and inferior arms 14, 16 are configured to laterally stabilize the spacer 10 with respect to the adjacent spinous processes 138, 140.

The spacer 10 is as easily and quickly removed from body of the patient as it is installed. The instrument 80 is inserted into an incision and reconnected to the spacer 10. The shaft 50 is rotated in the opposite direction via a driver 104 to fold the arms 14, 16 into a closed or undeployed configuration. In the undeployed configuration, the spacer 10 can be removed from the patient along with the instrument 80 or, of course, re-adjusted and re-positioned and then re-deployed as needed with the benefit of minimal invasiveness to the patient.

Any of the spacers disclosed herein are configured for implantation employing minimally invasive techniques including through a small percutaneous incision and through the supraspinous ligament. Implantation through the supraspinous ligament involves selective dissection of the supraspinous ligament in which the fibers of the ligament are separated or spread apart from each other in a manner to maintain as much of the ligament intact as possible. This approach avoids crosswise dissection or cutting of the ligament and thereby reduces the healing time and minimizes the amount of instability to the affected spinal segment. While this approach is ideally suited to be performed through a posterior or midline incision, the approach may also be performed through one or more incisions made laterally of the spine with or without affect to the supraspinous ligament. Of course, the spacer may also be implanted in a lateral approach that circumvents the supraspinous ligament altogether as well as in open or mini-open procedures.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

We claim:

1. An implant for placement between adjacent spinous processes in a spinal motion segment, the implant comprising:
   a body defining a longitudinal axis;
   a first arm rotatably connected to the body and including a pair of first extensions configured to receive a first spinous process between the first extensions to laterally stabilize the body with respect to the first spinous process when in a deployed configuration;
   and a second arm rotatably connected to the body and including a pair of second extensions configured to receive a second spinous process between the second extensions to laterally stabilize the body with respect to the second spinous process when in a deployed configuration; and
   wherein the first and second arms in a undeployed configuration are positioned for placement between adjacent spinous processes in which at least one of the adjacent spinous processes has a projection in a coronal plane that is angled with respect to a sagittal plane of the implant, wherein the implant operates to drive each of the first and second arms along a respective are of at least 90 degrees to rotate from the undeployed configuration to a deployed configuration such that the first and second extensions move away from the longitudinal axis and each other,
   wherein the first arm is pivotally coupled to the body such that the first extensions rotate together relative to the body to allow positioning of both of the first extensions on either side of the sagittal plane of the implant and positioning of the first spinous process between the first extensions when in the deployed configuration.

2. The implant of claim 1 further including a first bridge connected between the first extensions to define a first spinous process receiving portion.

3. The implant of claim 2 wherein the first extensions and first bridge are angled with respect to the sagittal plane of the implant.

4. The implant of claim 3 wherein the first bridge is substantially perpendicular to the first extensions.

5. The implant of claim 1 further including a first bridge connected between the first extensions to define a first spinous process receiving portion and a second bridge connected between the second extensions to define a second spinous process receiving portion.

6. The implant of claim 5 wherein the pair of first extensions is angled with respect to the sagittal plane of the implant and the pair of second extensions is angled with respect to the sagittal plane of the implant and the first and second bridges are perpendicular to their respective extensions to which they are connected.

7. The implant of claim 1 wherein the pair of first extensions is angled with respect to the sagittal plane of the implant and the pair of second extensions is angled with respect to the sagittal plane of the implant.

8. The implant of claim 1, wherein the first arm is configured to rotate from the undeployed configuration to the deployed configuration independent of a position of both of the first extensions which are located on one side of the sagittal plane of the implant.

9. The implant of claim 1, wherein an angle between a bridge of the first arm and the sagittal plane of the implant is locked by a drive tool prior to the first and second arms rotating from the undeployed configuration to the deployed configuration.

10. An implant for placement between adjacent spinous processes in a spinal motion segment comprising:
a body defining a longitudinal axis;
a first arm connected to the body, the first arm having a first pair of extensions defining a spinous process receiving portion for seating a superior spinous process therein; and
a second arm connected to the body, the second arm having a second pair of extensions defining a spinous process receiving portion for seating an inferior spinous process therein;
wherein at least one of the first arm or second arm is pivotally coupled to the body to allow the at least one of the first arm or second arm to move toward either side of a sagittal plane of the body, and a distance between the first pair of extensions is greater than a distance between the second pair of extensions,
wherein the implant is operable to move the first and second arms from an undeployed configuration to a deployed configuration to move the first pair of extensions and the second pair of extensions outwardly away from the longitudinal axis while at least one of first or second pair of extensions is positioned to one side of the sagittal plane.

11. The implant of claim 10 wherein the first pair of extensions are substantially parallel and the second pair of extensions are substantially parallel.

12. The implant of claim 10, wherein the first arm is a rigid shaped arm with a first bridge extending between the first pair of extensions, wherein the first arm is pivotally coupled to the body such that the first pair of extensions and the first bridge rotate together relative to the body to position the first pair of extensions on one side of the sagittal plane.

13. The implant of claim 10, wherein the first arm is movable relative to the body to adjust an angle between a bridge of the first arm and the sagittal plane of the implant, the bridge extends between the first pair of extensions, and wherein the first arm is configured to rotate from the undeployed configuration to the deployed configuration independent of the angle.

14. The implant of claim 10, wherein the first arm and/or the second arm rotates along an arc of at least 90 degrees from an undeployed configuration to a deployed configuration.

15. An implant for placement between adjacent spinous processes of a patient, the implant comprising:
a body defining a longitudinal axis and a sagittal plane;
a first U-shaped arm pivotally coupled to the body and including a pair of first extensions defining a first spinous process receiving portion for seating a first spinous process of the patient, the first U-shaped arm is configured to pivot relative to the body to a first position with both of the first extensions on a first side of the sagittal plane and to pivot relative to the body to a second position with both of the first extensions on a second side of the sagittal plane opposite the first side and the implant is configured, when the first U-shaped arm is pivoted to the first position or the second position, for locking the first U-shaped arm into the first position or the second position using a driving tool; and
a second U-shaped arm connected to the body and including a second pair of extensions defining a spinous process receiving portion for seating a second spinous process of the patient, the second U-shaped arm is configured to pivot relative to the body to a third position with both of the second extensions on a first side of the sagittal plane and to pivot relative to the body to a fourth position with both of the second extensions on a second side of the sagittal plane opposite the first side and the implant is configured, when the second U-shaped arm is pivoted to the third position or the fourth position, for locking the second U-shaped arm into the third position or the fourth position using the driving tool,
wherein the implant is operable to cause at least one of the first U-shaped arm or the second U-shaped arm to pivot from a undeployed configuration to a deployed configuration along an arc of at least 90 degrees.

* * * * *